US008131527B1

(12) United States Patent
Saxty et al.

(10) Patent No.: US 8,131,527 B1
(45) Date of Patent: Mar. 6, 2012

(54) FGFR PHARMACOPHORE COMPOUNDS

(75) Inventors: Gordon Saxty, Cambridge (GB);
Valerio Berdini, Cambridge (GB);
David Richard Newell, Northumberland (GB); Owen Callaghan, Den Bosch (NL); Maria Grazia Carr, Luton (GB);
Miles Stuart Congreve, Cambridge (GB); Adrian Liam Gill, Cheshire (GB);
Andrew Madin, Cambridge (GB);
Christopher William Murray, Cambridge (GB)

(73) Assignee: Astex Therapeutics Ltd., Cambridge (GB)

( * ) Notice: Subject to any disclaimer, the term of this patent is extended or adjusted under 35 U.S.C. 154(b) by 913 days.

(21) Appl. No.: 11/963,654

(22) Filed: Dec. 21, 2007

Related U.S. Application Data

(60) Provisional application No. 60/871,531, filed on Dec. 22, 2006, provisional application No. 60/979,577, filed on Oct. 12, 2007.

(51) Int. Cl.
*G06G 7/58* (2006.01)
*G01N 23/00* (2006.01)
*G01N 23/83* (2006.01)
(52) U.S. Cl. .............................. 703/11; 702/19; 702/27
(58) Field of Classification Search .................. None
See application file for complete search history.

(56) References Cited

U.S. PATENT DOCUMENTS

| | | | |
|---|---|---|---|
| 5,990,146 A | 11/1999 | Boschelli et al. | |
| 6,465,484 B1 | 10/2002 | Bilodeau et al. | |
| 2004/0019210 A1 | 1/2004 | Chivikas Connolly et al. | |
| 2004/0267510 A1* | 12/2004 | Bemis et al. .................. | 703/11 |

FOREIGN PATENT DOCUMENTS

| | | |
|---|---|---|
| EP | 1882475 A1 | 1/2008 |
| WO | 98/54093 | 12/1998 |
| WO | 00/12089 | 3/2000 |
| WO | 00/53605 | 9/2000 |
| WO | 02/12238 | 2/2002 |
| WO | 03/099811 | 12/2003 |
| WO | 2004/052286 | 6/2004 |
| WO | 2005/054230 | 6/2005 |
| WO | 2006/000420 | 1/2006 |
| WO | 2006/091671 | 8/2006 |
| WO | 2008/008747 | 1/2008 |
| WO | 2008/075068 | 6/2008 |

OTHER PUBLICATIONS

Mohammadi et al. "Structures of the Tyrosine Kinase Domain of Fibroblast Growth Factor Receptor in Complex with Inhibitors", Science, 1997, vol. 276, pp. 955-960.*
Fraley et al. "Synthesis and Initial SAR Studies of 3,6-Disubstituted Pyrazolo[1,5-a]pyrimidines: A New Class of KDR Kinase Inhibitors" Bioorganic & Medicinal Chemistry Letters 12 (2002) 2767-2770.
Wu et al. "Design and Synthesis of 3,7-diarylimidazopyridines as inhibitors of the VEGF-receptor KDR" Bioorganic & Medicinal Chemistry Letters 14 (2004) 90-912.
Bilodeau et al. "Design and Synthesis of 1,5-Diarylbenzimidazoles as Inhibitors of the VEGF-Receptor KDR" Bioorganic & Medicinal Chemistry Letters 13 (2003) 2485-2488.
Fraley et al. "Optimization of a Pyrazolo[1,5-a]pyrimidine Class of KDR Kinase Inhibitors: Improvements in Physical Properties Enhance Cellular Activity and Pharmacokinetics" Bioorganic & Medicinal Chemistry Letters 12 (2002) 3537-3541.
Skaper et al. "The FGFR1 inhibitor PD 173074 Selectively and Potently Antagonizes FGF-2 Neurotrophic and Neurotropic Effects" Journal of Neurochemistry, 75, (2000) 1520-1527.
Mohammadi et al. "Crystal Structure of an Angiogenesis Inhibitor Bound to the FGF Receptor Tyrosine Kinase Domain" The EMBO Journal, 1998 vol. 17 No. 20 (1998) pp. 5896-5904.
Connolly et al. "Discovery and Structure-Activity Studies of a Novel Series of Pyrido[2,3-d]pyrimidine Tyrosine Kinase Inhibitors" Bioorganic & Medicinal Chemistry Letters, 1997 vol. 7. No. 18 pp. 2415-2420.
Hamby et al. "Structure-Activity relationships for a Novel Series of Pyrido[2,3-d]pyrimidine Tyrosine Kinase Inhibitors" J. Med. Chem. 1997, 40, 2296-2303.

* cited by examiner

*Primary Examiner* — Suzanne M. Noakes
(74) *Attorney, Agent, or Firm* — Heslin Rothenberg Farley & Mesiti P.C.

(57) ABSTRACT

The present invention relates to FGFR pharmacophores, and in particular to compounds which are capable of binding to FGFR with greater affinity than their binding to VEGFR and methods of identifying such compounds using the pharmacophore. The present invention further relates to compositions, methods and uses of the compounds and the pharmacophores disclosed herein.

47 Claims, No Drawings

FGFR PHARMACOPHORE COMPOUNDS

CROSS REFERENCE TO RELATED APPLICATIONS

This application claims priority under 35 U.S.C. §119 to U.S. Provisional Application Nos. 60/871,531 filed Dec. 22, 2006 and 60/979,577 filed Oct. 12, 2007, which are both incorporated herein by reference.

FIELD OF THE INVENTION

The present invention relates to FGFR pharmacophores, and in particular to compounds which are capable of binding to FGFR with greater affinity than their binding to VEGFR and methods of identifying such compounds using the pharmacophore. The present invention further relates to compositions, methods and uses of the compounds and the pharmacophores disclosed herein.

BACKGROUND OF THE INVENTION

Protein Tyrosine Kinases (PTK)

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state (Powers, et al. (2000) Endocr. Relat. Cancer, 7, 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Ozawa, et al. (2001), Teratog. Carcinog. Mutagen., 21, 27-44).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Upon ligand binding, the receptors dimerize and auto- or transphosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2 (Lemonnier, et al. (2001), J. Bone Miner. Res., 16, 832-845). In addition, mutation screening in patients with syndromic craniosynostoses indicates that a number of recurrent FGFR2 mutations accounts for severe forms of Pfeiffer syndrome (Lajeunie et al, *European Journal of Human Genetics* (2006) 14, 289-298). Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al. (1996) Am. J. Hum. Genet., 58, 491-498; Plomp, et al. (1998) Am. J. Med. Genet., 75, 245-251), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2 (Yu, et al. (2000), Proc. Natl. Acad. Sci. U.S.A., 97, 14536-14541).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J. (2000), et al., Endocr. Rel. Cancer, 7, 165; Qiu, W. et. al. (2005), World Journal Gastroenterol, 11(34)). Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC) (Journal of Pathology (2007), 213 (1), 91-98). Increased expression was associated with mutation (85% of mutant tumors showed high-level expression) but also 42% of tumors with no detectable mutation showed over-expression, including many muscle-invasive tumors.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat, S., et al. (2002) The Journal of Clinical Investigation, 109, 1; Wang et al. (2004) Clinical Cancer Research, 10). In addition a germ-line polymorphism (Gly388Arg) is associated with increased incidence of lung, breast, colon and prostate cancers (Wang et al. (2004) Clinical Cancer Research, 10). In addition, a truncated form of FGFR4 (including the kinase domain) has also been found to present in 40% of pituitary tumours but not present in normal tissue.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006) Clin Cancer Res. 12(22): 6652-6662.

Rhabdomyosarcoma (RMS), the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes (Genes, Chromosomes & Cancer (2007), 46(11), 1028-1038).

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al. (1997 & 2002); Barrios, et al. (1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005). The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman (1997), 79, 1-81; Folkman (1995), *Nature Medicine*, 1, 27-31; Folkman and Shing (1992) *J. Biol. Chem.*, 267, 10931).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott (1992), *Ann. Rhum. Dis.*, 51, 919). In diabetes (and in many different eye diseases), new vessels invade the macula or retina or other ocular structures, and may cause blindness (Brooks, et al. (1994) *Cell*, 79, 1157). The process of atherosclerosis has been linked to angiogenesis (Kahlon, et al. (1992) *Can. J. Cardiol.*, 8, 60). Tumor growth and metastasis have been found to be angiogenesis-dependent (Folkman (1992), *Cancer Biol*, 3, 65; Denekamp, (1993) *Br. J. Rad.*, 66, 181; Fidler and Ellis (1994), *Cell*, 79, 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al. (1994) *Cell*, 79, 315; Ingber, et al. (1990) *Nature*, 348, 555), ocular diseases (Friedlander, et al. (1995) *Science*, 270, 1500), arthritis (Peacock, et al. (1992), *J. Exp. Med.*, 175, 1135; Peacock et al. (1995), *Cell. Immun.*, 160, 178) and hemangioma (Taraboletti, et al. (1995) *J. Natl. Cancer Inst.*, 87, 293).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al. (2000), *The Oncologist*, 5(90001), 1-2). VEGFR(s) are protein tyrosine kinases (PTKs). PTKs catalyze the phosphorylation of specific tyrosine residues in proteins involved in cell function thus regulating cell growth, survival and differentiation. (Wilks, A. F. (1990), *Progress in Growth Factor Research*, 2, 97-111; Courtneidge, S. A. (1993) *Dev. Suppl.*, 57-64; Cooper, J. A. (1994), *Semin. Cell Biol.*, 5(6), 377-387; Paulson, R. F. (1995), *Semin. Immunol.*, 7(4), 267-277; Chan, A. C. (1996), *Curr. Opin. Immunol.*, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. (1995), et al., *J. Cell Biol.*, 129, 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G. (2000), *The Oncologist*, 5(90001), 3-10).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angio genesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition Inhibition of VEGFR2 but not VEGFR1 markedly disrupted angiogenic switching, persistent angiogenesis, and initial tumor growth. In late-stage tumours, phenotypic resistance to VEGFR2 blockade emerged, as tumours regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

A FGF-trap adenovirus has been previously reported to bind and block various ligands of the FGF family, including FGF1, FGF3, FGF7, and FGF10, thereby effectively inhibiting angiogenesis in vitro and in vivo. Indeed, adding the FGF-trap treatment in the regrowth phase of a mouse model produced a significant decrease in tumor growth compared to anti-VEGFR2 alone. This decrease in tumor burden was accompanied by a decrease in angiogenesis that was observed as decreased intratumoral vessel density.

Batchelor et al. (Batchelor et al., 2007, *Cancer Cell*, 11(1), 83-95) provide evidence for normalization of glioblastoma blood vessels in patients treated with a pan-VEGF receptor tyrosine kinase inhibitor, AZD2171, in a phase 2 study. The rationale for using AZD2171 was based partially on results showing a decrease in perfusion and vessel density in an in vivo breast cancer model (Miller et al., 2006, *Clin. Cancer Res.* 12, 281-288). Furthermore, using an orthotopic glioma model, it had previously been identified that the optimal window of time to deliver anti-VEGFR2 antibody to achieve a synergistic effect with radiation. During the window of normalization, there was improved oxygenation, increased pericyte coverage, and upregulation of angiopoietin-1 leading to a decrease in interstitial pressure and permeability within the tumour (Winkler et al., 2004, *Cancer Cell* 6, 553-563). The window of normalization can be quantified using magnetic resonance imaging (MRI) using MRI gradient echo, spin echo, and contrast enhancement to measure blood volume, relative vessel size, and vascular permeability.

The authors showed that progression on treatment with AZD2171 was associated with an increase in CECs, SDF1, and FGF2, while progression after drug interruptions correlated with increases in circulating progenitor cells (CPCs) and plasma FGF2 levels. The increase in plasma levels of SDF1 and FGF2 correlated with MRI measurements, demonstrated an increase in the relative vessel density and size. Thus, MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3-(trifluoromethyl)phenyl)ureido)phenoxy)-N2-methylpyridine-2-carboxamide, targets both the Raf signalling pathway to inhibit cell proliferation and the VEGFR/PDGFR signalling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Mention is made of Mohammadi et al, (*Science*, 1997, vol 276, pp. 955-960) which describes the crystallisation of FGFR1 and Miyazaki et at (*Bioorg. Med. Chem. Lett.*, 2005, vol 15, pp. 2203-2207), which describes the crystallisation of VEGFR, both complexed with inhibitors bound.

SUMMARY OF THE INVENTION

Broadly, the present invention relates to the identification e.g. design or selection of modulators of FGFR, and especially FGFR1, FGFR2 and FGFR3 and/or FGFR4. The modulator compounds are capable of binding to FGFR and inhibiting its activity. Advantageously, the modulator compounds exhibit selectivity for FGFR tyrosine kinase over other tyrosine kinases in particular VEGFR2, and may be capable of binding to FGFR and inhibiting its activity in preference to binding to VEGFR and inhibiting its activity.

In a first aspect, the present invention provides a compound which is capable of binding to FGFR with greater affinity than VEGFR2 kinase and comprises a pharmacophore represented by Formula 1:

Formula 1 wherein

Group D is a chemical group containing an unsaturated (pi) system in which at least two of the atoms in Group D form a double, triple or aromatic bond; and W is any atom, whether as an atom in a ring system or not.

Features of such compounds are discussed in more detail below.

The invention further includes compounds where W may be carbon or a heteroatom such as N, O or S, attached to any functional group or molecular scaffold.

In a further aspect, the present invention provides the use of a compound as defined herein for the preparation of a medicament for the treatment of a condition mediated by FGFR activity. Examples of such conditions include cancer, angiogenesis, wound healing, human skeletal development and fibrotic conditions. The compounds of the invention may be particularly useful in the treatment of multiple myeloma, bladder, cervical, prostate and thyroid carcinomas, lung, breast, and colon cancers.

In a further aspect, the present invention provides a pharmaceutical composition comprising a compound as defined herein which is capable of binding to FGFR and a therapeutically acceptable carrier.

In a further aspect, the present invention provides a method of modulating FGFR activity in a mammal comprising administering to the mammal a therapeutically effective amount of a compound as defined herein, or a pharmaceutically acceptable salt or derivative thereof.

In a further aspect, the present invention provides a method of treating a condition mediated by FGFR activity in a mammal comprising administering to the mammal a therapeutically effective amount of a compound as defined herein or a pharmaceutically acceptable salt or derivative thereof.

In a further aspect, the present invention provides a method of identifying a compound which is a candidate modulator, such as an inhibitor, of FGFR having greater affinity for FGFR than for VEGFR2, the method comprising:

(a) designing and/or selecting a candidate modulator e.g. an inhibitor using the pharmacophore represented by Formula 1 or a compound as defined herein;

(b) fitting one or more candidate modulators to determine the probability of the candidate modulator interacting with FGFR; and (c) optionally modifying the candidate modulator based on the result of the fitting step.

In a further aspect, the present invention provides a method of identifying a compound which is a candidate modulator, such as an inhibitor, of FGFR having greater affinity for FGFR than for VEGFR2, the method comprising:

(a) designing and/or selecting or providing a candidate modulator e.g. an inhibitor comprising or containing the pharmacophore represented by Formula 1 or a compound as defined herein;

(b) fitting one or more candidate modulators to determine the probability of the candidate modulator interacting with FGFR
(c) optionally modifying the candidate modulator based on the result of the fitting step; and
(d) optionally identifying a candidate modulator which is capable of binding or modulating the FGFR; and In a further aspect, the present invention provides a method of identifying a compound which is a candidate modulator, such as an inhibitor, of FGFR having greater affinity for FGFR than for VEGFR2, the method comprising:
(a) providing a candidate modulator e.g. an inhibitor using the pharmacophore represented by Formula 1 or a compound as defined herein;
(b) fitting one or more candidate modulators to determine the probability of the candidate modulator interacting with FGFR;
(c) optionally modifying the candidate modulator based on the result of the fitting step; and
(d) optionally identifying a candidate modulator which is capable of binding or modulating FGFR.

In a further aspect, the present invention provides a method of identifying a compound which is a candidate modulator, such as an inhibitor, of FGFR having greater affinity for FGFR than for VEGFR2, the method comprising:
(a) designing and/or selecting or providing a candidate modulator e.g. an inhibitor comprising or containing the pharmacophore represented by Formula 1 or a compound as defined herein;
(b) fitting one or more candidate modulators to determine the probability of the candidate modulator interacting with FGFR
(c) optionally modifying the candidate modulator based on the result of the fitting step; and
(d) optionally identifying a candidate modulator which is capable of binding or modulating the FGFR; and
(d(ii)) optionally identifying a candidate modulator which is capable of binding or modulating VEGFR2 to a lesser extent.

In some embodiments of the invention, one or more of steps (a)-(c) are carried out in silico, e.g. using computer modelling as discussed in more details below.

Steps (b) and (c) can optionally be repeated in an iterative manner.

In one embodiment, step (b) comprises fitting one or more candidate modulators to determine the probability of the candidate modulator interacting with the residues of the binding cavity of FGFR, for example any of the residues described herein, for example those in Table 8 and the corresponding residues for other tyrosine kinases. In particular step (b) involves fitting of one or more candidate modulators to one or more of the FGFR residues outlined in Table 8.

In one embodiment, step (d) comprises identifying a compound which is capable of binding to FGFR by X-ray crystallography, NMR spectroscopy, ITC, thermal denaturation, Mass spectrometry or SPR as described herein. In another embodiment, step (d) comprises identifying a compound which is capable of modulating FGFR by use of an activity or functional assay as described herein.

The invention includes methods of designing and/or identifying a compound which is a candidate modulator of FGFR which involve the above described steps (a)-(c) and further involves the further step described above in (d(ii)).

In one embodiment, step (d(ii)) comprises identifying a compound which is less capable of binding to VEGFR2 by X-ray crystallography, ITC, thermal denaturation, NMR spectroscopy Mass spectrometry or SPR as described herein.

In another embodiment, step (d(ii)) comprises identifying a compound which is less capable of modulating VEGFR2 by use of an activity or functional assay as described herein.

In a further aspect, the present invention provides a method of designing and identifying a compound which is a modulators of FGFR having greater affinity for FGFR than for VEGFR2 which comprises, having identified a candidate modulator according to a method defined herein, the further steps of:
(e) obtaining or synthesising the candidate modulator; and/or
(f) contacting the candidate modulator with FGFR and/or VEGFR2 to determine the ability of the candidate modulator to interact with the FGFR and/or VEGFR2.

Therefore, the invention includes methods of designing and/or identifying a compound which are modulators of FGFR which involve the above described steps (a)-(c) and further involve the further steps described above in (e) and (f).

Step (f) may comprise contacting the candidate modulator with FGFR and/or VEGFR2 to determine the ability of the candidate modulator to interact with these tyrosine kinases under conditions to determine its function.

The method may also comprise one or more of the following steps:
(g) obtaining information about the binding of the candidate modulator to FGFR or VEGFR2; and
(h) adjusting the structure or functionality of the candidate modulator to improve binding to the binding cavity or cavities.

Step (g) may comprise obtaining structural information about the binding of the candidate modulator to FGFR or VEGFR2, for example, by X-ray crystallography, or may comprise obtaining biophysical information about the binding of the candidate modulator to FGFR or VEGFR2, for example, by NMR.

In a further aspect, the present invention provides a method for assessing the ability of a candidate modulator to interact with FGFR and/or VEGFR2, which comprises the steps of:
(a) obtaining or synthesising the candidate modulator;
(b) forming a complex of FGFR and/or VEGFR2 and said candidate modulator; and
(c) analysing said complex by a physical means to determine the ability of said candidate modulator to interact with FGFR and/or VEGFR2.

In some embodiments, this method for determining the binding of a candidate modulator to FGFR and/or VEGFR2 by its structure, may comprise the steps of:
(a) providing a crystal of FGFR and/or VEGFR2;
(b) soaking the crystal with the candidate modulator to form a complex; and
(c) determining the structure of the complex.

Known crystals and crystal structures of the kinase domain of FGFR and VEGFR2 which could be used in step (a) above and in the other methods described herein are discussed in the Section E.

Alternatively or additionally, the method for determining the binding of a candidate modulator to FGFR or VEGFR2 by it structure, may comprise the steps of:
(a) mixing said protein with said candidate modulator to form a protein-candidate modulator complex;
(b) crystallizing said protein-candidate modulator complex; and
(c) determining the structure of said protein-candidate modulator complex.

Alternatively, determining the binding of a candidate modulator to FGFR or VEGFR2 is carried out by physical means for example ITC, thermal denaturation, Mass spectrometry, SPR or NMR spectroscopy.

In the methods described herein, the method may comprise repeating one or more of the steps set out in the methods defined herein, e.g. steps (a) to (h) above, one or more times.

In a further aspect, the present invention provides a method of identifying a compound which is an inhibitor of FGFR having greater affinity for FGFR than for VEGFR2, the method comprising:
 a) determining the FGFR activity of the compound; and
 b) determining the VEGFR2 activity of the compound.

It will be appreciated that steps a) and b) in the above method can be performed in either order.

In a further aspect, the present invention provides a method of identifying a compound that exhibits selectivity for FGFR over VEGFR2, the method comprising:
 a) determining the FGFR activity of the compound; and
 b) determining the VEGFR2 activity of the compound It will be appreciated that steps a) and b) in the above method can be performed in either order.

The FGFR and VEGFR2 activities, in particular the tyrosine kinase enzyme activities, can be determined as described herein or using methods known to a person skilled in the art. In particular, the method comprises determining the FGFR or VEGFR2 activity of the compound under conditions to determine its function for example using a kinase activity bioassay. One such bioassay is described herein.

Therefore, in a further aspect, the present invention provides a method of identifying a compound which is an inhibitor of FGFR having greater affinity for FGFR than for VEGFR2, the method comprising:
 a) determining the FGFR tyrosine kinase activity of the compound by contacting the compound with the protein under conditions to determine its kinase activity; and
 b) determining the VEGFR2 tyrosine kinase activity of the compound by contacting the compound with the protein under conditions to determine its kinase activity.

In a further aspect, the present invention provides a method of designing a compound which is an inhibitor of FGFR having greater affinity for FGFR than for VEGFR2, the method comprising:
 a) determining the FGFR activity of the compound;
 b) determining the VEGFR2 activity of the compound; and
 c) modifying the compound structure so as to alter the activity for VEGFR2 or FGFR.

The step of modifying the compound structure so as to alter the activity for VEGFR2 or FGFR can utilise the publicly available crystal structures of these kinases or other methods known to a person skilled in the art.

In particular these methods are used to design or identify compounds which have at least 10 fold selectivity for FGFR over VEGFR2 or which have 10 fold greater affinity for FGFR than for VEGFR2

A further aspect of the invention is a compound so identified i.e. a compound which is capable of binding to FGFR with greater affinity than VEGFR2 kinase.

A further aspect of the invention is a compound that exhibits selectivity for FGFR over VEGFR2.

A further aspect of the invention is a compound capable of binding to FGFR and inhibiting its activity in preference to binding to VEGFR and inhibiting its activity.

In some instances, the methods may comprise, following identification of a compound, the step of:
 (i) manufacturing the compound or preparing a pharmaceutical composition comprising the compound.

In a further aspect, the present invention provides a method of making a pharmaceutical composition comprising admixing such an inhibitor with a pharmaceutically acceptable excipient, vehicle or carrier, and optionally other ingredients.

In a further aspect, the present invention provides a method for preparing a medicament, pharmaceutical composition or drug, the method comprising:
 (a) identifying a FGFR candidate modulator according to a method as defined herein;
 (b) optimising the structure of said candidate modulator; and
 (c) preparing a medicament, pharmaceutical composition or drug containing the optimised candidate modulator.

The method may further comprise optimising the structure of the FGFR candidate modulator, this comprises one or more of the following steps:
 (i) adding molecular scaffolding; and/or
 (ii) adding or varying functional groups; and/or
 (iii) connecting the candidate modulator with other molecules such that the chemical structure of the candidate modulator is changed while its original modulating functionality is maintained or enhanced.

The method may further comprise optimising the structure of the FGFR candidate modulator, this comprises one or more of the following steps:
 (i) adding molecular scaffolding to the candidate modulator containing the pharmacophore of Formula 1; and/or
 (ii) adding or varying functional groups; and/or
 (iii) connecting the candidate modulator with other molecules such that the chemical structure of the candidate modulator is changed while its original modulating functionality is maintained or enhanced.

In a further aspect, the present invention provides the use of a pharmacophore as defined in Formula 1 for the screening or development of FGFR modulators, which have greater affinity for FGFR, in particular FGFR1-4 such as FGFR1-3, than VEGFR.

In a further aspect, the present invention provides a method of determining whether a chemical not previously known to be a modulator of FGFR is capable of specifically modulating FGFR to a greater extent than it modulates VEGFR2 comprising:
 (a) selecting compounds containing the pharmacophore of Formula 1;
 (b) contacting FGFR with a chemical to be tested under conditions such that the chemical can interact with the FGFR;
 (c) detecting the binding and/or modulation of the chemical to the FGFR; and
 (d) identifying chemicals which are capable of binding or modulating FGFR more than VEGFR2.

In a further aspect, the present invention provides a method of determining whether a chemical not previously known to be a selective modulator of FGFR is capable of specifically modulating FGFR comprising:
 (a) selecting compounds containing the pharmacophore of Formula 1;
 (b) contacting FGFR with a compound selected or provided in step (a) under conditions such that the chemical can interact with the FGFR;
 (c) detecting the binding and/or modulation of the chemical to the FGFR; and
 (d) identifying chemicals which are capable of selectively binding or modulating the FGFR.

Identifying chemicals which are capable of binding or modulating FGFR more than VEGFR2 can be carried out by biophysical means including, for example X-ray crystallography, ITC, thermal denaturation, Mass spectrometry, SPR or NMR spectroscopy, or activity means including for example bioassay, as described herein.

In a further aspect, the present invention provides a method of preparing a composition which comprises determining whether a chemical not previously known to be a modulator of FGFR has the property of modulating an FGFR more than VEGFR2 and admixing the chemical with a carrier to provide the composition.

In a further aspect, the present invention provides use of a pharmacophore as defined in Formula 1 for selecting candidate modulators of FGFR which have greater affinity for FGFR than VEGFR2, which (a) are capable of binding to FGFR, and/or (b) are capable of modulating an activity of FGFR, and/or (c) inhibit the FGFR activity of FGFR to a greater extent than they (a) are capable of binding to VEGFR2, and/or (b) are capable of modulating an activity of VEGFR2, and/or (c) inhibit the activity of VEGFR2.

In a further aspect, the present invention provides use of a pharmacophore as defined in Formula 1 for designing and identifying compounds which have greater affinity for FGFR than VEGFR2, which (a) are capable of binding to FGFR, and/or (b) are capable of modulating an activity of FGFR, and/or (c) inhibit the FGFR activity of FGFR to a greater extent than they (a) are capable of binding to VEGFR2, and/or (b) are capable of modulating an activity of VEGFR2, and/or (c) inhibit the activity of VEGFR2.

In one embodiment, the present invention provides a method for designing compounds which bind to FGFR to a greater extent than it binds to VEGFR2 comprising the steps of:
(a) selecting one of the molecular scaffolds of Example 1-15, such as Examples 1-12; and
(b) optimising the structure of the candidate modulator to increase its binding to FGFR, and/or
(c) optimising the structure of the candidate modulator to decrease its binding to VEGFR2.

In a further aspect, the present invention provides a computer-based method for the analysis of the interaction of a candidate modulator with FGFR and/or VEGFR2, which comprises:
(a) providing the structure of the FGFR or VEGFR2 comprising a three-dimensional representation of FGFR or VEGFR2 or portion thereof;
(b) providing a candidate modulator based on Formula 1 to be fitted to said FGFR or VEGFR2 structure; and
(c) fitting the candidate modulator to the FGFR or VEGFR2 structure of (a)

In a further aspect, the present invention provides a computer-based system containing one or more of the following:
(a) the pharmacophore information of Formula 1; and/or
(b) a structure of a candidate molecule as defined above fitted into the structure of FGFR or VEGFR2; and/or
(c) the coordinate information of the candidate modulator-FGFR or candidate modulator-VEGFR2 complex.

In further aspects, the present invention provides a computer programmed to carry out the method as described herein, a computer program for carrying out the method as described herein and data carriers having a program saved thereon for carrying out a method as described herein.

Embodiments of the present invention will now be described in more detail by way of example and not limitation with reference to the accompanying examples. In the description of features of the present invention, it is intended that, unless the context expressly requires otherwise, the features of the invention are disclosed independently of each other and that the present invention encompasses all combinations of these features.

DEFINITIONS

By "FGFR" we mean FGFR1, FGFR2, FGFR3 and FGFR4, in particular FGFR1, FGFR2, and FGFR3, more particularly FGFR1 or FGFR3.

By 'binding to FGFR with greater affinity than VEGFR2 kinase' or 'candidate modulators, such as inhibitors, of FGFR having greater affinity for FGFR than for VEGFR2' we mean a compound having greater affinity, binding, activity against or inhibition of FGFR in particular FGFR1, FGFR2, FGFR3 than VEGFR2.

By 'selective FGFR inhibitor' or 'exhibit selectivity for FGFR tyrosine kinase over other tyrosine kinases in particular VEGFR2' we mean a compound having greater affinity, binding, activity against or inhibition of FGFR in particular FGFR1, FGFR2, FGFR3 than other tyrosine kinases in particular VEGFR2.

In particular the candidate modulators have at least 10 times greater affinity, binding, activity against or inhibition of FGFR in particular FGFR1, FGFR2, FGFR3 than VEGFR2. Preferably the candidate modulators have at least 100 times greater affinity, binding, activity against or inhibition of FGFR in particular FGFR1, FGFR2, FGFR3 than VEGFR2. This can be determined using the methods described herein.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

In the following by "binding site" or "binding cavity" we mean a site (such as an atom, a functional group of an amino acid residue or a plurality of such atoms and/or groups) in the FGFR or VEGFR2 binding cavity, which may bind to an agent compound such as a candidate modulator e.g. an inhibitor. Depending on the particular molecule in the cavity, sites may exhibit attractive or repulsive binding interactions, brought about by charge, and/or steric considerations and the like.

Binding sites are sites within a macromolecule such as a tyrosine kinase, or on its surface, at which ligands can bind. Examples are the catalytic or active site of an enzyme (the site on an enzyme at which the amino acid residues involved in catalysing the enzymatic reaction are located), allosteric binding sites (ligand binding sites distinct from the catalytic site, but which can modulate enzymatic activity upon ligand binding), cofactor binding sites (sites involved in binding/coordinating cofactors e.g. metal ions), or substrate binding sites (the ligand binding sites on a protein at which the substrates for the enzymatic reaction bind). There are also sites of protein-protein interaction. More particularly binding sites of FGFR and VEGFR2 are defined herein as including those residues outlined in Tables 1-3.

In the following by "active site" we mean a site (such as an atom, a functional group of an amino acid residue or a plurality of such atoms and/or groups) in FGFR binding cavity, which is involved in catalysis. In particular this refers to the active site residues, for example either ASP641 or ALA564 in FGFR1.

The term "hydrogen bond" refers to a favourable interaction that occurs whenever a suitable donor atom, $Q^X$, bearing a proton, H, and a suitable acceptor atom, $Q^Y$, have a separation of <3.5 Å and where the angle $Q^X$-H-$Q^Y$ is greater than 90 degrees. Sometimes, a single acceptor atom $Q^Y$ may form a plurality of hydrogen bonds with a plurality of protons on suitable donor atoms, $Q^X$. Sometimes, a single proton on a donor atom $Q^X$ may form hydrogen bonds with a plurality of suitable acceptor atoms, $Q^Y$. For example, the proton on a —NH-group may form a separate hydrogen bond with each of the two oxygen atoms in a carboxylate anion. Suitable donor and acceptor atoms are well understood in medicinal chemistry (G. C. Pimentel and A. L. McClellan, The Hydrogen Bond, Freeman, San Francisco, 1960; R. Taylor and O. Kennard, Hydrogen Bond Geometry in Organic Crystals, Accounts of Chemical Research, 17, pp. 320-326 (1984)).

The term "hydrogen bond donor" refers to a chemical structure containing a suitable hydrogen bond donor atom bearing one or more protons. It refers to a group having a hydrogen atom capable of forming a hydrogen bond with acceptor atom in the same or an adjacent molecule; see for example "*Advanced Organic Chemistry*" by Jerry March, 4$^{th}$ edition, pages 75-79 and references therein. Examples of donor atoms having one proton are —NH, C—NH$_2$, C—NH, C—OH, C—SH, or aromatic C—H. Examples of donor atoms having more than one proton are —NH$_2$, —[NH$_3$]$^+$ and [NH$_4$]$^+$.

The term "hydrogen bond acceptor" refers to a chemical structure containing a suitable hydrogen bond acceptor atom. It refers to a group capable of forming a hydrogen bond with a hydrogen atom in the same or an adjacent molecule; see for example "*Advanced Organic Chemistry*" by Jerry March, 4$^{th}$ edition, pages 75-79 and references therein. Examples of acceptor atoms include fluorine, oxygen, sulfur and nitrogen and thus in the present context, hydrogen bond acceptors include nitrogen, oxygen and sulphur atoms; and groups containing nitrogen, oxygen and sulphur atoms.

The term "lipophilic" or "hydrophobic" refers to a non-polar moiety that tends not to dissolve in water and is fat-soluble. Hydrophobic moieties include, but are not limited to, hydrocarbons, such as alkanes, alkenes, alkynes, cycloalkanes, ethers, cycloalkenes, cycloalkynes and aromatic compounds, such as aryls, certain saturated and unsaturated heterocycles, and moieties that are substantially similar to the side chains of lipophilic natural and unnatural amino acids, including valine, leucine, isoleucine, methionine, phenylalanine, α-amino isobutyric acid, alloisoleucine, tyrosine, and tryptophan. Lipophilic interactions can be modeled using a variety of means. For example the ChemScore function (Eldridge M D; Murray C W; Auton T R; Paolini G V; Mee R P Empirical scoring functions: I. The development of a fast empirical scoring function to estimate the binding affinity of ligands in receptor complexes, *Journal of computer-aided molecular design* (1997 September), 11(5), 425-45) assigns protein and ligand atoms as hydrophobic or polar, and a favorable energy term is specified for the interaction between two hydrophobic atoms. Other methods of assessing the hydrophobic contributions to ligand binding are available and these would be known to one skilled in the art.

"Polar" refers to compounds having one or more polar bonds in which the electron density of the bond lies closer to one atom than the other as one of the atoms is more electronegative than the other. This means that one of the atoms develops a degree of positive charge while the other some degree of negative charge. Compounds having polar bonds generally have dipole moments. In contrast, covalent bonds between atoms having the same electronegativity are symmetric.

"Acidic" refers to the tendency of compounds to donate a proton (H$^+$) (Bronsted-Lowry Theory) or accept an electron pair into an empty orbital (Lewis Theory of Acids and Bases).

"Basic" refers to the tendency of compounds to accept a proton (H$^+$) (Bronsted-Lowry Theory) or donate an electron pair (Lewis Theory of Acids and Bases).

By "fitting", is meant determining by automatic, or semi-automatic means, interactions between one or more atoms of a candidate molecule and at least one atom of a tyrosine kinase structure e.g. FGFR1, FGFR2, FGFR3, FGFR4, VEGFR2, and calculating the extent to which such interactions are stable. Interactions include attraction and repulsion, brought about by charge, and/or steric considerations and the like. Interactions of this type can be modeled computationally. An example of such computation would be via a force field such as Amber (Cornell et al. A Second Generation Force Field for the Simulation of Proteins, Nucleic Acids, and Organic Molecules, *Journal of the American Chemical Society*, (1995), 117(19), 5179-97) which would assign partial charges to atoms on the protein and ligand and evaluate the electrostatic interaction energy between a protein and ligand atom using the Coulomb potential. The Amber force field would also assign van der Waals energy terms to assess the attractive and repulsive steric interactions between two atoms. Other methods of assessing interactions are available and would be known to one skilled in the art of designing molecules consistent with specified pharmacophores. Various computer-based methods for fitting are described further herein.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Where reference is made herein to carbocyclic and heterocyclic groups, the carbocyclic or heterocyclic ring can, unless the context indicates otherwise, be unsubstituted or substituted by one or more substituents for example molecular fragments, a molecular scaffolds or functional groups as discussed herein.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, CC or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cyclohexenyl, cycloheptenyl and cyclooctenyl. Saturated heterocyclic groups include piperidine, morpholine, thiomorpholine. Partially saturated heterocyclic groups include pyrazolines, for example 2-pyrazoline and 3-pyrazoline.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. One further example of a five membered heteroaryl group includes thiadiazole.

Examples of six membered heteroaryl groups include but are not limited to pyridine, pyrazine, pyridazine, pyrimidine and triazine.

A bicyclic heteroaryl group may be, for example, a group selected from:
 a) a benzene ring fused to a 5- or 6-membered ring containing 1, 2 or 3 ring heteroatoms;
 b) a pyridine ring fused to a 5- or 6-membered ring containing 1, 2 or 3 ring heteroatoms;
 c) a pyrimidine ring fused to a 5- or 6-membered ring containing 1 or 2 ring heteroatoms;
 d) a pyrrole ring fused to a 5- or 6-membered ring containing 1, 2 or 3 ring heteroatoms;
 e) a pyrazole ring fused to a 5- or 6-membered ring containing 1 or 2 ring heteroatoms;
 f) an imidazole ring fused to a 5- or 6-membered ring containing 1 or 2 ring heteroatoms;
 g) an oxazole ring fused to a 5- or 6-membered ring containing 1 or 2 ring heteroatoms;
 h) an isoxazole ring fused to a 5- or 6-membered ring containing 1 or 2 ring heteroatoms;
 i) a thiazole ring fused to a 5- or 6-membered ring containing 1 or 2 ring heteroatoms;
 j) an isothiazole ring fused to a 5- or 6-membered ring containing 1 or 2 ring heteroatoms;
 k) a thiophene ring fused to a 5- or 6-membered ring containing 1, 2 or 3 ring heteroatoms;
 l) a furan ring fused to a 5- or 6-membered ring containing 1, 2 or 3 ring heteroatoms;
 m) an oxazole ring fused to a 5- or 6-membered ring containing 1 or 2 ring heteroatoms;
 n) an isoxazole ring fused to a 5- or 6-membered ring containing 1 or 2 ring heteroatoms;
 o) a cyclohexyl ring fused to a 5- or 6-membered ring containing 1, 2 or 3 ring heteroatoms; and
 p) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole). Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indo line, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups. One further example of a bicyclic heteroaryl group containing a six membered ring fused to a five membered ring includes imidazopyridine.

Particular examples of bicyclic heteroaryl groups containing two fused six membered rings include but are not limited to quinoline, isoquino line, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquino line, tetrahydroquino line, dihydrobenzthiene, dihydrobenzfuran, 2,3-dihydro-benzo[1,4]dioxine, benzo[1,3]dioxole, 4,5,6,7-tetrahydrobenzofuran, indo line and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indo linyl.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include saturated groups such as piperidine, pyrrolidine, azetidine, morpholine, piperazine and N-alkyl piperazines.

In a nitrogen-containing non-aromatic heterocyclic ring the ring must contain at least one ring nitrogen atom. The heterocyclic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclic groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclic groups can be polycyclic fused ring systems or bridged ring systems such as bicycloalkanes, tricycloalkanes and their oxa- and aza analogues (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

The heterocyclic groups can each be unsubstituted or substituted by one or more substituent groups. For example, heterocyclic groups can be unsubstituted or substituted by 1, 2, 3 or 4 substituents. Where the heterocyclic group is monocyclic or bicyclic, typically it is unsubstituted or has 1, 2 or 3 substituents.

Molecular fragments or molecular scaffolds are typically compounds with a molecular weight between 100 and 300 Da. They typically will have simple functional groups, for example those involving only carbon, nitrogen, oxygen, sulfur and halogens, and be more soluble than larger molecules. They are discussed in more detail in the following references Carr, R; et al.; Drug Discov. Today, 2002, 7(9):522-527; Bemis G W, et al.; J Med Chem. 1996, 39(15):2887-93; Bemis G W, et al.; J Med Chem. 1999; 42(25):5095-9; Fejzo J, et al.; Chem Biol. 1999; 6(10):755-69; Ajay, et al.; J Med Chem. 1999; 42(24):4942-51.

A functional group is a particular group of atoms in a molecule. They are submolecular structural motifs, characterized by specific elemental composition and connectivity, that confer reactivity upon the molecule that contains them. Just as elements have distinctive properties, functional groups have characteristic chemistries. Types of functional groups are discussed in standard chemistry textbooks such as March's Advanced Organic Chemistry: Reactions, Mechanisms and Structure by Michael Smith and Jerry March (John Wiley & Sons Inc) 1992 and 2001; Organic Chemistry by McMurry (Brooks Cole), Foundations of Organic Chemistry, Stephen G. Davies (Foreword), M. Hornby and Josephine Peach (Oxford Chemistry Primers, Oxford University Press) 1993 etc.

The term "modulator" is a compound that will modulate FGFR activity i.e. increase or decrease the activity of FGFR. Modulators of FGFR may be inhibitors of the enzyme or compounds which affect their specificity or activity in relation to their respective substrates in other ways. The invention is particularly suitable for the design, selection and development of FGFR inhibitor components e.g. FGFR inhibitor compounds. The present invention therefore particularly pertains to modulators that decrease the activity of the FGFR i.e. that the modulators are FGFR inhibitors.

The term "pharmaceutical composition" is used herein to define a solid or liquid composition in a form, concentration and level of purity suitable for administration to a patient (e.g. a human or animal patient) upon which administration it can elicit the desired physiological changes.

By a "computer system" we mean the hardware means, software means and data storage means used to analyse atomic coordinate data. The minimum hardware means or device of the computer-based systems of the present invention typically comprises a central processing unit (CPU), input means or device, output means or device and data storage means or device. Desirably a monitor is provided to visualise structure data. The data storage means or device may be RAM or means or device for accessing computer readable media of the invention. Examples of such systems are microcomputer workstations available from Silicon Graphics Incorporated and Sun Microsystems running Unix based, Windows NT or IBM OS/2 operating systems.

By "computer readable media" we mean any medium or media, which can be read and accessed directly by a computer e.g. so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

By "optimising the structure" we mean e.g. adding molecular scaffolding, adding or varying functional groups, or connecting the molecule with other molecules (e.g. using a fragment linking approach) such that the chemical structure of the modulator molecule is changed while its original modulating functionality is maintained or enhanced. Such optimisation is regularly undertaken during drug development programmes to e.g. enhance potency, promote pharmacological acceptability, increase chemical stability etc. of lead compounds.

DETAILED DESCRIPTION

A. FGFR Tyrosine Kinase Modulators and Pharmacophores

Described herein are compounds that bind to FGFR tyrosine kinases, and in particular FGFR 1, FGFR 2, FGFR 3 or FGFR 4 more particularly FGFR 1-3, which may advantageously act as therapeutically useful inhibitors, that interact with the protein or proteins in the active site by binding to the catalytic FGFR kinase pocket residues (Glu562 Ala564-hinge—and Asp641 in FGFR1 numbering from PDB file 1AGW (Mohammadi et al) and also optionally to adjacent sub-pockets in the active site region, according to the following specified pharmacophoric interactions.

The pharmacophore provided herein is particularly advantageous as it provides compounds with greater activity against FGFR than VEGFR2 kinase.

The compounds exemplified in this invention bind to FGFR tyrosine kinases but may not always have biological activity in an enzyme assay, and therefore will be useful as starting points for structure guided optimisation in order to derive larger, more functionalised compounds that are enzyme inhibitors, useful ligands, and therapeutically useful agents.

B. Detailed Description of the Pharmacophore

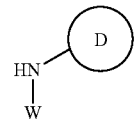

Formula 1

Formula 1 illustrates the pharmacophore of the invention. The Group D is a chemical group containing an unsaturated (pi) system in which at least two of the atoms in Group D form a double, triple or aromatic bond.

In one embodiment, the unsaturated (pi) system is linked to the NH group via a —CH$_2$-linker.

In a preferred embodiment, the atom connecting group D to the NH bond has at least one double or aromatic bond with the other atoms in D. The connecting atom in group D would then be sp2 hybridised, the hybridisation of atoms in the formation of bonds being a well known concept in organic chemistry (Introduction to Organic Chemistry, Streitwieser and Heathcock, Second Edition, pp 22-26, Macmillan Publishing Co.).

In the pharmacophore of Formula 1, W is any atom, whether as an atom in a ring system or not. W may be carbon or a heteroatom such as N, O or S. Where W is carbon, the carbon atom may be sp3, sp2 or sp hybridised and hence attached to any group by a single, double or triple bond.

The pharmacophore of the invention contains an uncharged or charged amine. This interacts with one or both of the Asp641 carbonyl oxygens (FGFR1 1AGW PDB code numbering) through a hydrogen bond. The amine group has at least one hydrogen in order to be able to interact with Asp641. Examples of uncharged amines occur in amides, ureas and anilines. Examples of charged amines are amidines.

Particular examples of D include acyclic pi systems such as acyclic double bonds including alkenes, carbonyls (e.g. C(=O)R), amides, esters, sulphonyl and sulphonamides groups, triple bonds such as alkynes or nitriles, and cyclic double bonds e.g. partially saturated carbocyclic or heterocyclic rings, aromatic carbocyclic rings, heteroaromatic rings or unsaturated ring containing exocyclic pi systems.

Particular examples of the pharmacophore of Formula 1 and their proposed binding modes are detailed below in Formula 2-6 below for clarity. The dotted line ----- in ring systems exemplified in Formula 3-6, and subgroups thereof, can represent a single, or double or aromatic bond. The arrows in Formula 2-6 represent possible interactions between the moieties drawn.

Preferred cyclic groups are partially saturated or aromatic 5 membered ring containing a donor NH, CH or S in the 2 position with an acceptor N, O or a carbonyl, sulphonyl in the 4 position.

In one embodiment of Formula 1 the pi system may be a six-membered aromatic ring. Examples of the NH-pi system of Formula 1 where the pi system is a six-membered ring are laid out below in Table 1.

TABLE 1

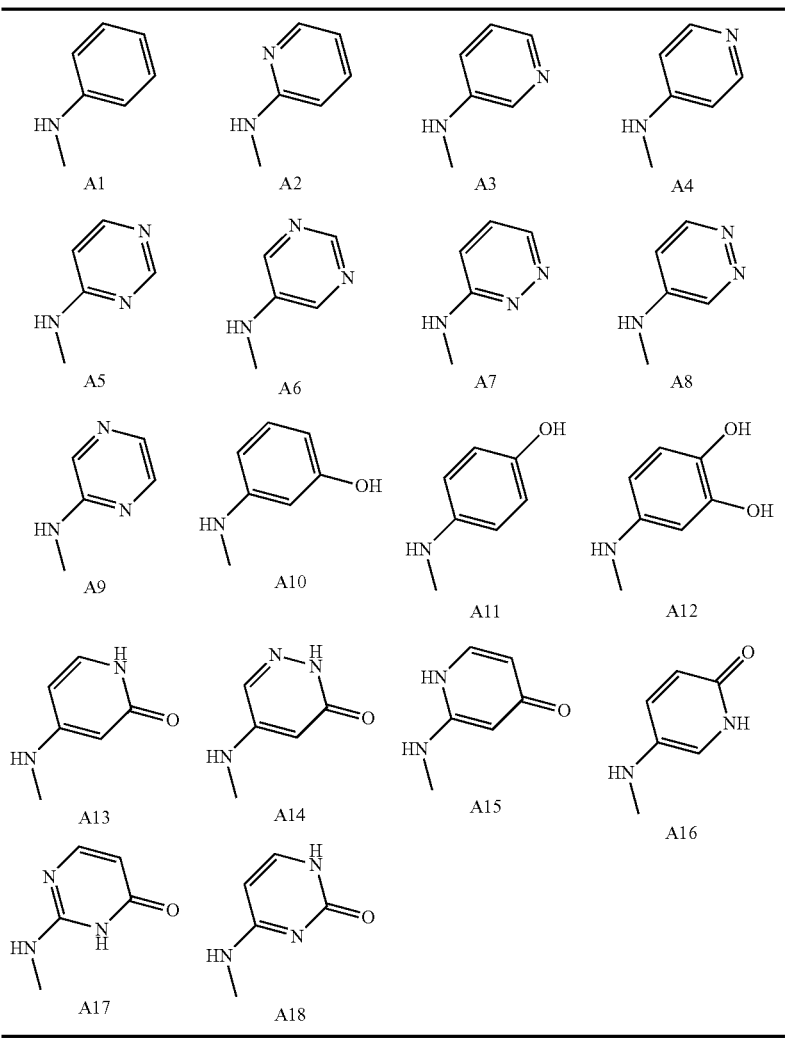

Particular examples of NH-D include A1, A4 and A9.

When the unsaturated (pi) system is linked to the NH group via a —CH$_2$— linker, one example of an aromatic ring system encompassed by the pi system is shown in the following formula A19:

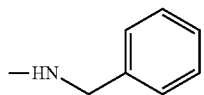

A19

In a further embodiment the Group D is a 5 membered ring, in particular a 5-membered heteroaromatic ring.

Particular examples of the NH-D of Formula 1 where the pi system is a five-membered ring are laid out below in Table 2.

TABLE 2

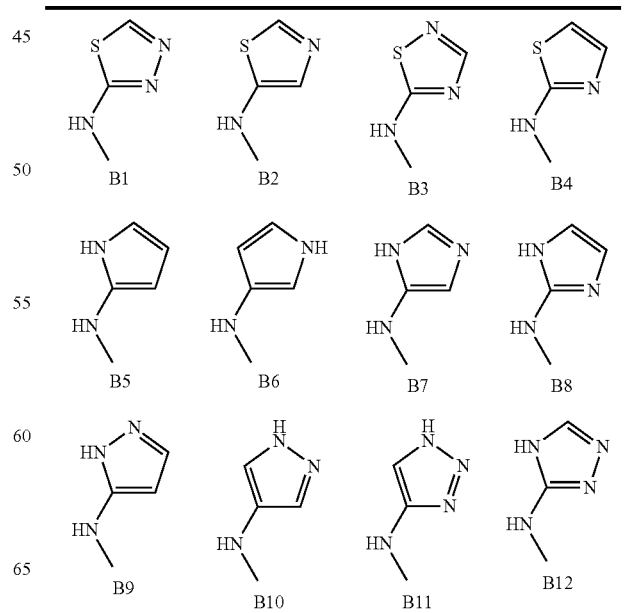

TABLE 2-continued

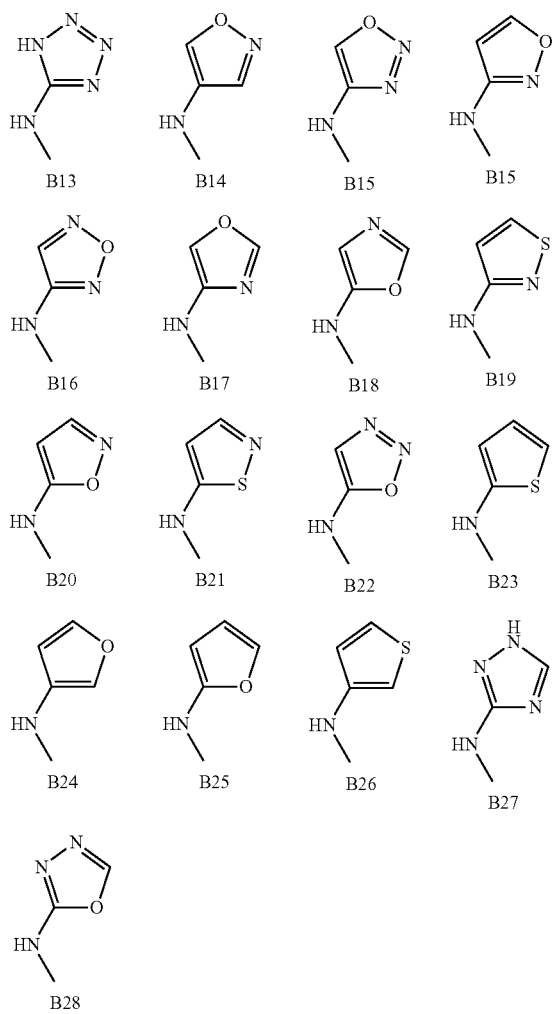

Particular examples of NH-D include B1-26. Further particular examples of NH-D are B1-3, B4, B6, B7, B9-18, B20-22, B24 and B26.

Preferred example of the pharmacophore of Formula 1 is laid in Formula 2A wherein Group D are 5-membered heteroaromatic rings as shown in Formula 2B:

Formula 2A

Formula 2B

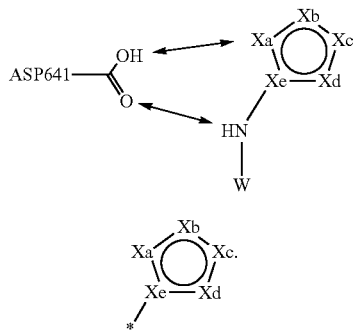

wherein
Xa is selected from NH, CH, and S;
Xb is selected from C, N, O, and S;

Xc is selected from N and O;
Xd is selected from C, N, O and S;
Xe is selected from C and N.
and * represents point of attachment to NH In one embodiment the pharmacophore is of Formula 2A.

Particular examples of Formula 2B include nitrogen-containing heterocyclic groups in particular nitrogen-containing heteroaromatic rings such as thiadiazole e.g. 1,3,4-thiadiazole and triazoles.

Alternatively the pharmacophore of Formula 1 is laid in Formula 3A wherein Group D can be a carbocyclic or heterocyclic ring with an exocyclic double bond, as laid out below in Formula 3B.

Formula 3A

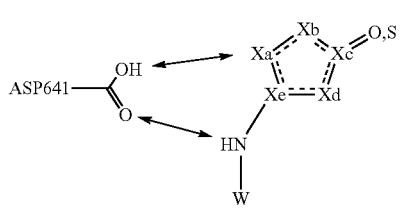

Formula 3B

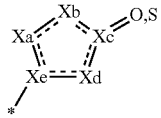

wherein the dotted line ==== can represent a single, or double bond.
Xa is selected from NH, CH, and S;
Xb is selected from C, N, O, and S;
Xc is selected from C, S and N;
Xd is selected from C, N, O, and S;
Xe is selected from C and N.
and * represents point of attachment to NH In one embodiment the pharmacophore is of Formula 3A.

Particular examples of Group D include saturated, partially-saturated or aromatic rings with exocyclic carbonyls or sulphonyls. Particular examples of the NH-D of Formula 1 where the Group D is an unsaturated ring containing exocyclic pi systems, are laid out below in Table 3.

TABLE 3

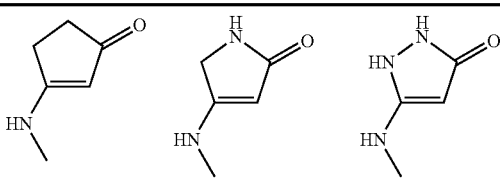

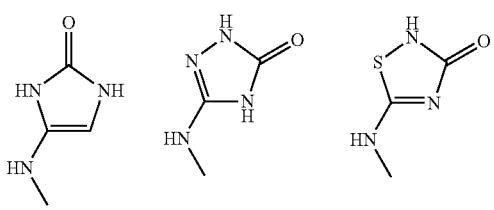

TABLE 3-continued

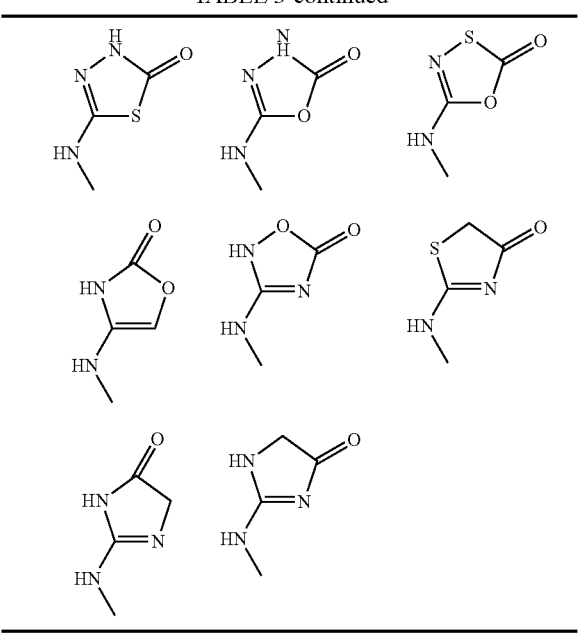

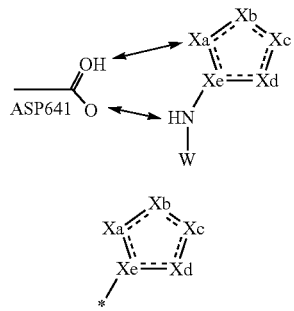

Formula 4A wherein the dotted line ≡ can represent a single, or double bond.
Xa is selected from NH, CH, and S;
Xb is selected from C, N, O, and S;
Xc is selected from C, N, O and S;
Xd is selected from C, N, O, and S;
Xe is selected from C and N.
and * represents point of attachment to NH In another embodiment the pharmacophore is of Formula 4A, wherein Group D is a partially-saturated ring as shown Formula 4B. Particular examples include nitrogen containing rings.

In another embodiment the pharmacophore is of Formula 5A or Formula 6A. Particular acyclic examples of Group D, are laid out below in Formula 5B and Formula 6B.

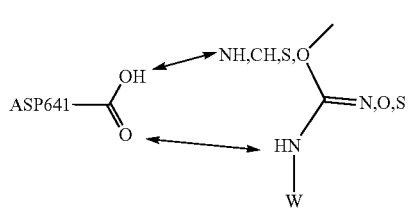

Formula 5A

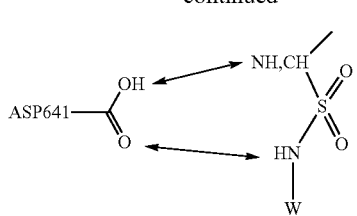

Formula 6A

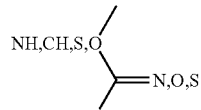

Formula 5B

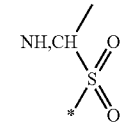

Formula 6B

It will be clear to a person skilled in the art that the open bond from the NH, CH, S, O or CH, NH groups in the above pharmacophore formulas represents a bond to any atom (such as to result in a chemically feasible compound) and includes H.

In one embodiment the pharmacophore is of Formula 5A.
Particular examples of Formula 5A include acyclic double bonds such as ureas, thioureas, amides, thioamides, carbamates, thiocarbamates e.g. O-substituted thiocarbamates or S-substituted thiocarbamates, dithiocarbamates, amidines, guanidines, isoureas, and isothioureas. One further example includes CH2 linked groups such as a —CH$_2$—CONRR group (wherein R may represent any suitable substituent).

Preferred examples of Formula 5A are detailed below in Table 4.

TABLE 4

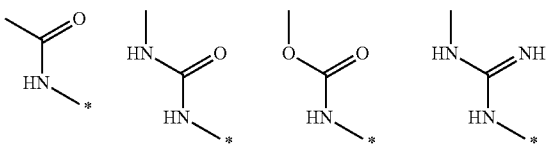

* is point of attachment to W

Preferred examples are amides, carbamates and ureas, in particular ureas.

In one embodiment the pharmacophore is of Formula 6A.
Particular examples of acyclic pi systems of Formula 6A include sulfamate, thiosulfamate, sulfonamides and sulfonylureas.

Preferred examples of Formula 6A are detailed below in Table 5.

TABLE 5

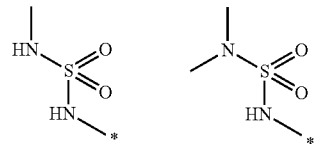

* is point of attachment to W

In a further embodiment the pi system D is a carbon-carbon double bond e.g. alkene, or a triple bond e.g. a nitrile or an alkyne.

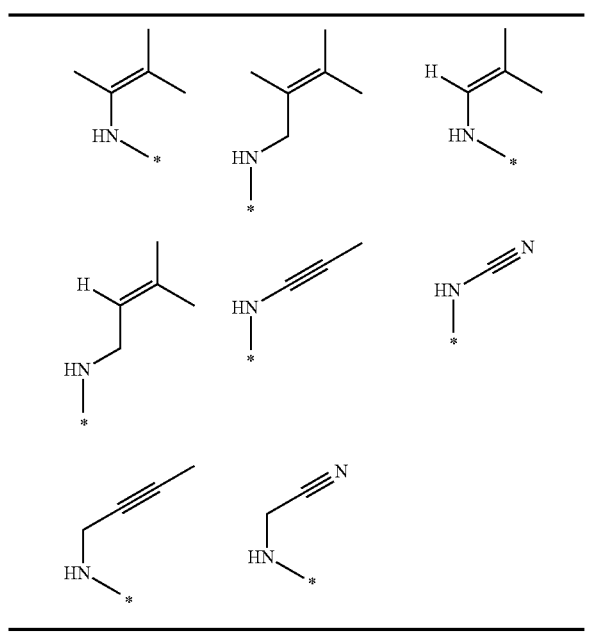

* is point of attachment to W?

This pharmacophore of Formula 1, and subgroups thereof, includes where molecular scaffolds or fragments or functional groups are added or attached to the pharmacophore. In particular these can be added at positions outlined below.

B. Particular Embodiments of Formula I

On one embodiment the molecular scaffolds or fragments or functional groups are added or attached to the pharmacophore of Formula 1, and subgroups thereof. In particular molecular scaffolds or fragments or functional groups added at W. In one particular embodiment W is the groups A and B as outlined in Formula 8 below.

Formula 8 illustrates a particular embodiment of the pharmacophore of the invention and illustrates an exemplary binding mode of compounds of the invention, for clarity.

Formula 8

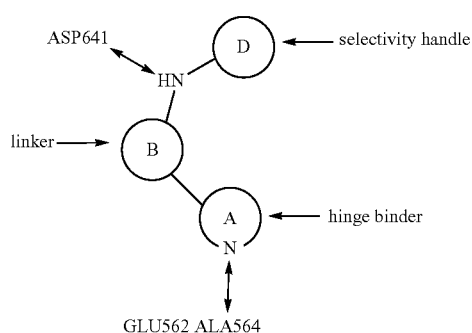

Ring A - mono or bicyclic heteroaromatic
Ring B - nonaromatic or aromatic ring
Group D - pi-system The formula 8 illustrates up to 2 hydrogen bonding interactions of the hinge binder with the Ala564 backbone (NH and C=O) and potentially another one with the Glu562 (backbone C=O). In formula 8 a further two hydrogen bonding interactions may be formed with the carboxylic acid (of residue Asp641). It is, of course, possible that not all of the interactions, outlined above, and illustrated in Formula 8, will be formed by all compounds suitable for use in this invention but preferred compounds will at least contain one hydrogen bond to the carboxylic acid of Asp641 and a hydrogen bond to the backbone N—H of Ala564.

Ring A

In Formula 8, the Ring A is formed by aromatic atoms (can be C, N, O and S) forming a mono or a polycyclic aromatic system such as a 5 to 12 membered ring containing at least a hydrogen bond acceptor.

The compounds of the invention in particular have an aromatic mono-cyclic or bicyclic heterocycle group, Ring A, containing at least one acceptor that forms a hydrogen bond with the backbone N—H of Ala564 and optionally contains donors to interact with either or both backbone C=O's of Ala564 and Glu562 (hinge region). Examples of hydrogen bond acceptors and examples of Ring A are detailed below.

Ring A is a bicyclic heterocyclic group having 8 to 12 ring members of which up to 5 are heteroatoms selected from O, N and S or a monocyclic heterocyclic group having 4 to 7 ring members of which up to 4 are heteroatoms selected from O, N and S.

Examples of bicyclic and monocyclic, heterocyclic groups are as set out above in the General Preferences and Definitions section.

In one embodiment Ring A is a bicyclic heterocyclic group having 8 to 12 ring members of which up to 5 are heteroatoms selected from O, N and S.

Typically, the bicyclic group A has 8 to 10 ring members for example 9 or 10 ring members.

In one embodiment, the bicyclic group A is an optionally substituted bicyclic heteroaryl group.

Examples of bicyclic heteroaryl groups include pyridine or pyrimidine rings fused to a 5- or 6-membered carbocyclic or heterocyclic aromatic ring. Particular examples of such a group are the imidazo[1,2-a]pyridine, or 1H-pyrrolo[2,3-b]pyridine.

In another embodiment Ring A is a monocyclic heterocyclic group having 4 to 7 ring members of which up to 4 are heteroatoms selected from O, N and S.

Typically, the monocyclic group A has 4 to 6 ring members for example 5 or 6 ring members.

In one embodiment, the monocyclic group A is an optionally substituted monocyclic heteroaryl group.

In one embodiment, the bicyclic or monocyclic group A may take the form shown below:

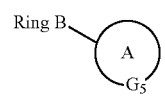

where G5 is a hydrogen bond acceptor atom or group.

Particular examples of hydrogen bond acceptors are the groups set out in Table 5 below.

TABLE 5

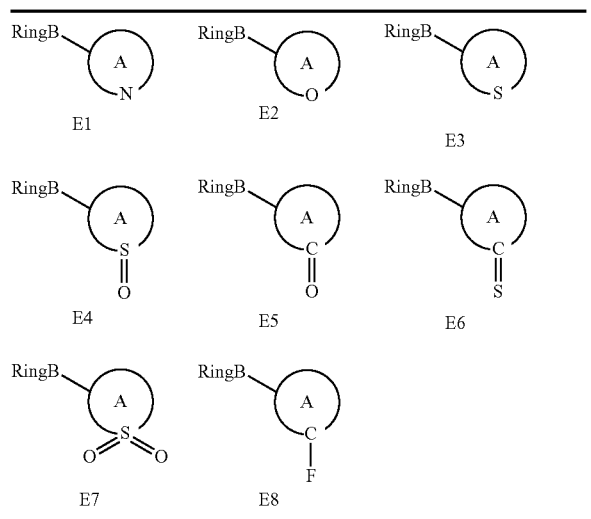

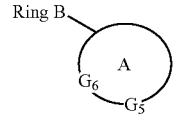

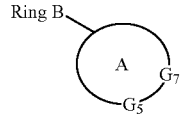

Particular examples of Ring A are where the hydrogen bond acceptors are N or C=O as in E1 and E5 above.

In one embodiment ring A is E1 or E5.

A cyclic group A may contain one hydrogen bond acceptor, or more than one (e.g. two or three) hydrogen bond acceptor moieties.

The cyclic group A may contain a hydrogen bond donor group adjacent to the group G5 and hence the cyclic group A may take the form:

where G5 is a hydrogen bond acceptor atom or group and G6 or G7 is a hydrogen bond donor group.

The hydrogen bond donor group can be, for example, NH, C—NH$_2$, C—NH, C—OH, C—SH, or aromatic C—H. In particular the hydrogen bond donor group is NH and aromatic C—H. In addition the cyclic group A may contain a further hydrogen bond donor moiety. The further hydrogen bonding moiety may be on the same ring as the hydrogen bonding donor and/or acceptor for example in a monocyclic Ring A, or on a second fused ring to the ring containing the hydrogen bind donor and/or acceptor in a bicyclic Ring A. In particular the further hydrogen bond donor group is NH and aromatic C—H.

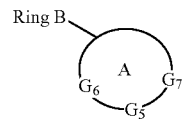

Particular examples of Ring A are set out in Table 6.

TABLE 6

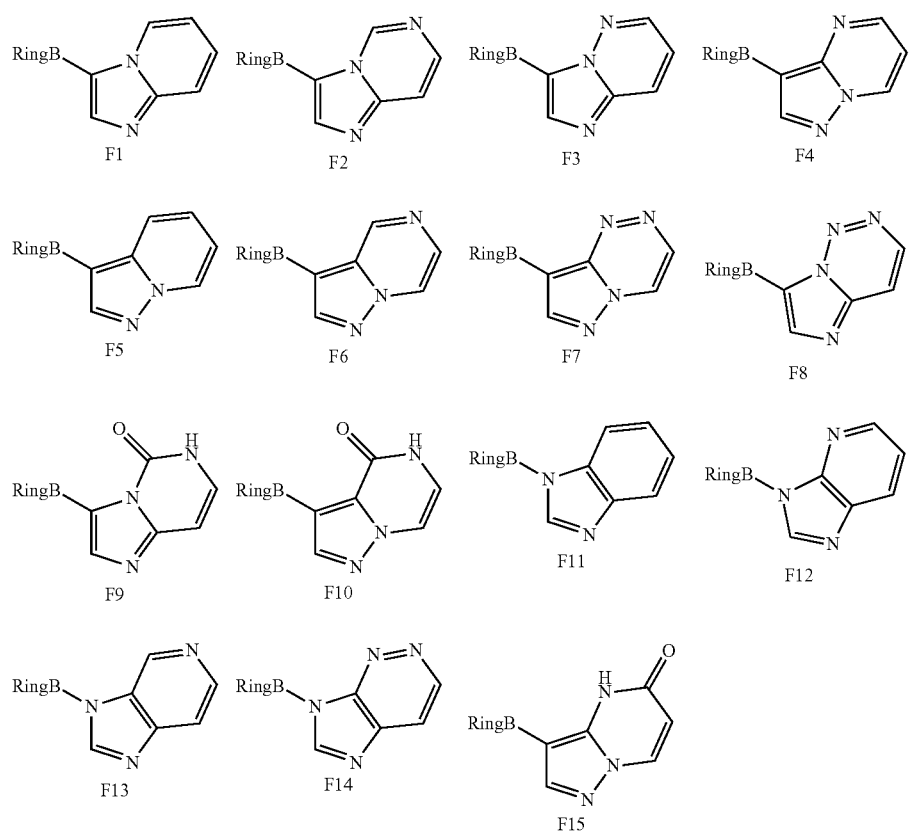

33

Particular Ring A groups include F1-F12.

Particularly preferred Ring A groups are F1-F6.

Ring B

Ring B connecting the hinge binder Ring A with the amine group, described below. This 'Ring B' system is held in place between a group of hydrophobic interactions with residue's side chains (Val492, Ala512, Lys514 carbon chain, Val561, Leu630, Ala640).

Ring B is a non-aromatic or aromatic carbocyclic or heterocyclic group. Such a ring system may be a saturated ring system but is preferably an aromatic ring system. Ring B can have 5-12 ring members as defined herein and maybe a monocyclic or a bicyclic group. In one embodiment Ring B is monocyclic aromatic ring having for example a 5- or 6- or 7-membered ring. In another embodiment Ring B has 5 or 6 ring members in particular 6 ring members. Ring B can be a carbocyclic or heterocyclic ring, but in particular an aromatic carbocycle such as phenyl.

Particular examples of Ring B and, examples of connectivity patterns to Ring A and NH-D, are shown below in Table 7.

34

One further example of Ring B and, examples of connectivity patterns to Ring A and NH-D, is as follows:

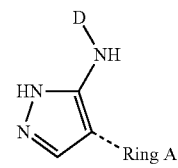

In one embodiment, where Ring B is aromatic, the amine forms an aniline group.

In the context of Ring B, in a preferred embodiment the amine group is positioned on the Ring B such that it is spaced apart from the point attachment to Ring A by 1 or 2 intervening atom. In one particular embodiment, there is 1 intervening atom.

TABLE 7

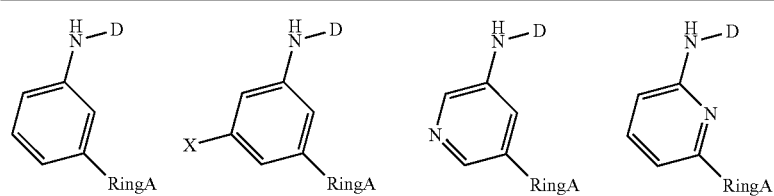

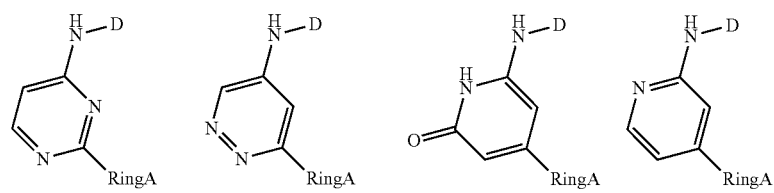

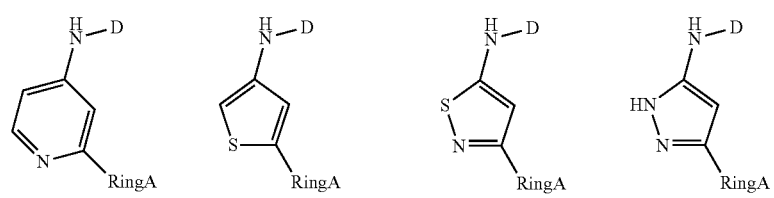

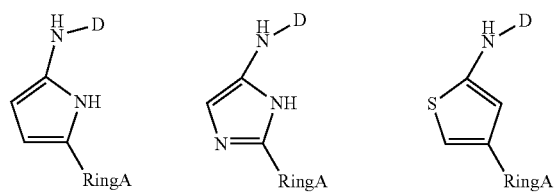

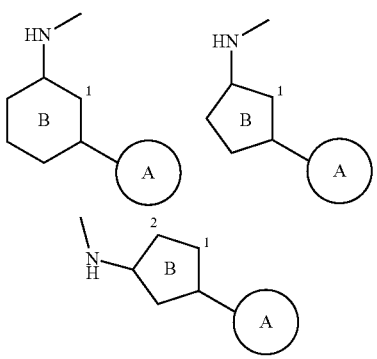

By way of explanation, in the substructures shown above, it is preferred that there are one or two intervening atoms (labelled 1 and 2) between the point of attachments of Ring A and the amine.

In particular where Ring B is a 6 membered ring the NH group is on the 3 (meta) position of the Ring B with respect to the Ring A.

In particular where Ring B is a 5 membered ring the NH group is on the 3 or 4 position of the Ring B with respect to the Ring A.

The intervening atom(s) can be carbon atoms (as shown in the substructures above) or they can be heteroatoms.

Additional Functionality Y and Z

This pharmacophore of Formula 8, and subgroups thereof, includes where molecular scaffolds or fragments or functional groups are added or attached to the pharmacophore. In particular these can be added at positions Y and Z as outlined below in Formula 9.

Formula 9

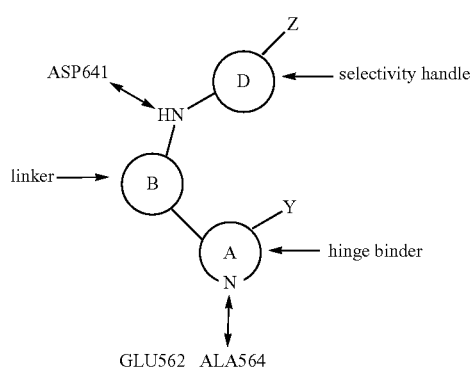

Using the information provided herein, and available to a person skilled in the art, appropriate functionality to add at positions Y and Z can be designed and chosen to increase affinity to FGFR and/or further decrease affinity to VEGFR. Such design would be driven by the method of structure-based design where existing knowledge on the 3D arrangement of atoms in the active site of FGFR1 (PDB code: 1AGW (Mohammadi et al, *Science,* 1997, vol 276, pp. 955-960), and VEGFR2 (PDB Code: 1YWN (Miyazaki et al, *Bioorg. Med. Chem. Lett.,* 2005, vol 15, pp. 2203-2207) would be used in conjunction with experimental verification of affinities to iteratively improve the affinity for FGFR and improve or maintain the selectivity over VEGFR2. Such design would be known to one skilled in the art using the information contained herein.

Excluding from consideration any atoms or groups that may form part of the hydrogen acceptor G5 where present, the cyclic group A may be an unsubstituted ring system (Y is no group) or a substituted ring system.

In formula 9, Y in particular can be selected from no group and optionally substituted carbocyclic and heterocyclic rings. Examples of carbocyclic and heterocyclic groups are set out above in the General Preferences and Definitions section. Optional substitution of Y would include the addition of solubilising groups.

In one embodiment, where Ring A is an optionally substituted monocyclic, the carbocyclic and heterocyclic Y group is a bicyclic ring system.

In another embodiment where Ring A is bicyclic, the carbocyclic and heterocyclic groups Y are monocyclic. Typical monocyclic Y groups can have 4-7 ring members in particular 5-6 ring members.

In one embodiment the carbocyclic and heterocyclic groups are saturated. Preferably the carbocyclic and heterocyclic groups are aromatic.

In particular Z can be no group, small groups or a solubilising group.

C. Binding in Active Site Region

Using the pharmacophore of Formula 1 alternative compounds comprising formulas 1-8 can be designed using the structural and SAR information available. In particular a compound comprising Formula 1 could be designed wherein affinity for FGFR is obtained by interacting with the binding site of FGFR1. The group W can be designed using any of the range of structure-based discovery techniques described herein.

The key binding pockets of the FGFR kinase domain binding site are outlined in Table 8 (see for example, Buijsman, Structural aspects of kinases and their inhibitors in Methods and Principles in Medicinal Chemistry (2004), 22 (Chemogenomics in Drug Discovery), 191-219. Publisher: Wiley-VCH Verlag GmbH & Co. KGaA).

TABLE 8

| FGFR1 and VEGFR2 binding pocket and comparison | | |
|---|---|---|
| Binding pocket | FGFR1 (residue numbering from PDB file: 1AGW) | VEGFR2 (residue numbering from PDB file: 1YWN) |
| Hinge | Glu562, Tyr563, Ala564, Ser565 | Glu915, Phe916, Cys917, Lys918 |
| gatekeeper | Val561 | Val914 |
| Hydrophobic residues | Val492, Ala512, Lys514, Leu630, Ala640 | Val846, Ala864, Lys866, Leu1033, Cys1043 |
| DFG loop | Asp641, Phe642, Gly643 | Asp1044, Phe1045, Gly1046 |
| Glycine Rich Loop (GRL) | Leu484, Gly485, Glu486, Gly487, Cys488, Phe489 | Leu838, Gly839, Arg840, Gly841, Ala842, Phe843. |
| Solvent Exposed Area | Lys 482, Leu484, Tyr563, Ser565, Lys566, Gly567, Glu571 | Lys836, Leu838, Phe916, Lys918, Phe919, Gly920, Thr924 |

The pharmacophore of Formula 8 provides molecules that have a hinge binding motif (Ring A), a linker (Ring B) to a donor nitrogen and a pi system (Group D) all as described above that are suitable for binding in the pockets specified in Table 8.

In a further embodiment alternative groups are designed for binding in the pockets specified in Table 8 to link to the pharmacophore of Formula 1.

Compounds that are capable of binding to the hinge region of FGFR and to the Asp641 of the DFG loop are preferred.

The 3-dimensional pharmacophore points of Table 9, each interacting with a region of the protein binding pocket, are used to define the type of functionality preferred for each pocket defined in Table 8. The points are described as weighted average positions in three-dimensional space. The distances between each pharmacophore point and the three-dimensional coordinates of the C-α atom of selected protein residues are reported in Table 9 for the enzyme FGFR1 (PDB code: 1AGW). These distances specify a position in three-dimensional space in the binding pocket that one skilled in the art could locate by examining the three-dimensional structure of FGFR1. The descriptions of the pharmacophore points define the type of interactions with the protein that are to be made at each of the positions.

TABLE 9

Pharmacophoric points

| Pharmacophoric points | Description | Distances from specified C-α atoms of FGFR1 (1AGW PDB Structure) | | |
|---|---|---|---|---|
| P_NH | H-bond to Asp641 Carboxylate | ASP641 5.3 Å | ASN628 6.8 Å | ILE545 8.5 Å |
| P_G5 | H-Bond to Ala564 backbone NH | ALA564 3.6 Å | LEU484 7.5 Å | ALA512 5.5 Å |
| P_D | Pi system favoured for FGFR | ALA640 6.2 Å | LEU630 7.1 Å | ASN628 5.9 Å |
| P_B | Gatekeeper region | VAL561 7.7. Å | ASP641 7.0 Å | LEU630 8.3 Å |
| P_G7 (Optional) | H-Bond to Ala564 backbone C=O | ALA564 4.5 Å | GLY567 4.9 Å | LEU484 6.9 Å |
| P_G6 (Optional) | H-Bond to Glu562 backbone C=O | GLU562 5.6 Å | ALA512 5.2 Å | LEU630 6.8 Å |
| P_Y (Optional) | Solvent exposed area | GLY567 4.5 Å | LEU484 6.1 Å | GLU571 9.1 Å |

Table 10 gives examples of the substituents that are preferred at each of the pharmacophore points together with tolerances that reflect how close the substituent must be to the specified pharmacophore point in order to make the required interaction. Preferably the substituent will be within this tolerance and most preferably within half the value of this tolerance.

TABLE 10

Preferred types of substituents for each pharmacophore point and the associated tolerance.

| Pharmacophoric points | Description | Type of Substituent | Tolerance |
|---|---|---|---|
| P_NH | H-bond to Asp 641 Carboxylate | NH | 1 Å |
| P_G5 | H-Bond to Ala564 backbone NH | Hydrogen Bond Acceptor (preferred Aromatic N) | 1 Å |
| P_D | Pi system | sp or sp2 hybridization (preferred sp2) | 2 Å |
| P_B | Gatekeeper region | Aromatic or lipophilic | 2 Å |
| P_G7 (Optional) | H-Bond to Ala564 backbone C=O | Hydrogen Bond Donor (Preferred Aromatic CH or NH) | 1 Å |
| P_G6 (Optional) | H-Bond to GLU562 backbone C=O | Hydrogen Bond Donor (Preferred Aromatic CH or NH) | 1 Å |
| P_Y (Optional) | Solvent exposed area | Lipophilic or aromatic or polar | 2 Å |

Compounds need not satisfy all the pharmacophore points but preferred compounds will meet first four pharmacophore points (P_NH, P_G5, P_D and P_B) in Table 10, and the most preferred compounds will additionally satisfy one, two or all of the optional pharmacophore points (P_G6, PG7 and P_Y).

The pharmacophore points specified in Table 10 can be used to design potent FGFR inhibitors which are VEGFR2 selective using standard docking, fitting and design methodology as outlined in the sections below. Additionally knowledge of the 3D structure of the active site of FGFR1 and VEGFR2 will allow one skilled in the art of structure based drug design to suggest further enhancements to the design of compounds by using standard methodologies. Such enhanced compounds would still satisfy the pharmacophore of Table 10 but would either be designed to increase potency against FGFR by making additional favourable interactions or be designed to decrease potency against VEGFR2 by making additional unfavourable interactions.

It is well known that there is often protein loop movement when inhibitors bind to enzymes and that, in particular, the glycine rich loop and DFG loop are known to be flexible in kinases (see for example, Buijsman 2004). Such movement may generate further interactions which could influence selectivity against VEGFR and affinity for FGFR. The normal iterative operation of structure-based drug design would allow the incorporation of such movements into the design process.

D. Structure-Based Drug Design

Determination of the FGFR pharmacophore can greatly assist the process of rational drug design. This information may be used for rational design of FGFR inhibitors, e.g. by computational techniques which identify possible binding ligands for the binding sites, by linked-fragment approaches to drug design, and by structure-based design based on the location of bound ligand. These techniques are discussed in more detail below.

Greer et al. (*J. of Medicinal Chemistry*, Vol. 37, (1994), 1035-1054) describes an iterative approach to ligand design based on repeated sequences of computer modelling, protein-ligand complex formation and X-ray crystallographic or NMR spectroscopic analysis. Thus novel thymidylate synthase inhibitor series were designed de novo by Greer et al., and FGFR inhibitors may also be designed in the this way. More specifically, using e.g. GRID on the solved 3D structure of the FGFR or VEGFR2, a ligand (e.g. a candidate modulator in particular an inhibitor) for FGFR may be designed that complements the functionalities of FGFR binding sites and/or does not complement the VEGFR2 binding sites. The ligand can then be synthesised, formed into a complex with the FGFR, and the complex then analysed by X-ray crystallography to identify the actual position of the bound ligand. The structure and/or functional groups of the ligand can then be adjusted, if necessary, in view of the results of the X-ray analysis, and the synthesis and analysis sequence repeated until an optimised ligand is obtained. Related approaches to structure-based drug design are also discussed in Bohacek et al., Medicinal Research Reviews, Vol. 16, (1996), 3-50.

Structure-based drug design and in silico approaches to drug design require accurate information on the atomic coordinates of target enzymes or receptors. The structures of several tyrosine kinase have been solved including the kinase domains of FGFR1 and 2 and VEGFR2, are available in the PDB (H. M. Berman, J. Westbrook, Z. Feng, G. Gilliland, T. N. Bhat, H. Weissig, I. N. Shindyalov, P. E. Bourne: The Protein Data Bank. *Nucleic Acids Research*, 28 pp. 235-242 (2000), http://www.rcsb.org/pdb/). Their PDB codes, for example, are 1AGW, 1FGK, 1FGI, 2FGI for FGFR1, 1GJO and 1OEC for FGFR2, and 1VR2, 1Y6A, 1Y6B and 1YWN for VEGFR2. Preferred PDB codes are those for FGFR1, for example including 1AGW, or those for VEGFR2, for example including 1YWN.

The structures of the kinase domains for FGFRs whose structures have not yet been solved can be obtained by homology modelling based on the structures of kinase domains of other tyrosine kinases, in particular FGFR1 and 2.

The co-ordinates used in the design, selection and analysis of the candidate modulators comprising Formula (I) obtained in the invention can be crystal structures for examples obtained from the PDB or obtained in house, or homology models. Homology models can be generated using "homology modelling". By "homology modelling", it is meant the prediction of structures for example of FGFR3 and FGFR4, based either on X-ray crystallographic data (for example of tyrosine kinase domains) or computer-assisted de novo prediction of structure, based upon manipulation of the coordinate data of existing tyrosine kinase domain structures. Homology modelling as such is a technique that is well known to those skilled in the art (see e.g. Greer, Science, Vol. 228, (1985), 1055, and Blundell et al., Eur. J. Biochem, Vol. 172, (1988), 513). The techniques described in these references, as well as other homology modelling techniques, generally available in the art, may be used in performing the present invention.

Homology modelling comprises the steps of: (a) aligning a representation of an amino acid sequence of a target protein of unknown three-dimensional structure with the amino acid sequence of the known protein to match homologous regions of the amino acid sequences; (b) modelling the structure of the matched homologous regions of said target protein of unknown structure on the corresponding regions of the known structure; and (c) determining a conformation for said target protein of unknown structure which substantially preserves the structure of said matched homologous regions. In particular one or all of steps (a) to (c) are performed by computer modelling.

The term "homologous regions" describes amino acid residues in two sequences that are identical or have similar (e.g. aliphatic, aromatic, polar, negatively charged, or positively charged) side-chain chemical groups. Identical and similar residues in homologous regions are sometimes described as being respectively "invariant" and "conserved" by those skilled in the art.

In general, the method involves comparing the amino acid sequence of proteins of unknown structure with the proteins of known structure by aligning the amino acid sequences (Dunbrack et al., Folding and Design, 2, (1997), 27-42). Amino acids in the sequences are then compared and groups of amino acids that are homologous (conveniently referred to as "corresponding regions") are grouped together. This method detects conserved regions of the polypeptides and accounts for amino acid insertions or deletions. Homology between amino acid sequences can be determined using commercially available algorithms. The programs BLAST, gapped BLAST, BLASTN, PSI-BLAST and BLAST 2 sequences (provided by the National Center for Biotechnology Information) are widely used in the art for this purpose, and can align homologous regions of two amino acid sequences.

Once the amino acid sequences of the polypeptides with known and unknown structures are aligned, the structures of the conserved amino acids in a computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions may be assigned manually by using standard peptide geometries or by molecular simulation techniques, such as molecular dynamics. The final step in the process is accomplished by refining the entire structure using molecular dynamics and/or energy minimization.

The aspects of the invention described herein which utilise the X-ray crystal structure of FGFR in silico for example the co-ordinates of FGFR1 and/or FGFR2 may be equally applied to homologue models of FGFR for example of FGFR3 and/or FGFR4 obtained by homology modelling using the co-ordinates of FGFR1 and/or FGFR2.

Linked-fragment approaches to drug design could also be used to design compounds comprising the pharmacophore. The fragment-linking approach involves determining (computationally or experimentally) the binding locations of plural ligands to a target molecule, and then constructing a molecular scaffold to connect the ligands together in such a way that their relative binding positions are preserved. The ligands may be provided computationally and modelled in a computer system, or provided in an experimental setting, wherein, for example, X-ray crystallography is used to determine their location. The pharmacophore of Formula I could be considered to be one such fragment for use in a linked fragment approach.

The binding site of two or more ligands are determined and may be connected to form a potential lead compound that can be further refined using e.g. the iterative technique of Greer et al. For a virtual linked-fragment approach see Verlinde et al., *J. of Computer-Aided Molecular Design*, 6, (1992), 131-147, and for NMR and X-ray approaches see Shuker et al., *Science*, 274, (1996), 1531-1534 and Stout et al., *Structure*, 6, (1998), 839-848. The use of these approaches with the pharmacophore of the invention can be used to design FGFR inhibitors.

Many of the techniques and approaches to structure-based drug design described above rely at some stage on X-ray analysis to identify the binding position of a ligand in a ligand-protein complex. A common way of doing this is to perform X-ray crystallography on the complex, produce a difference Fourier electron density map, and associate a particular pattern of electron density with the ligand. However, in order to produce the map (as explained e.g. by Blundell, T L and Johnson, L N, in *Protein Crystallography*, Academic Press, New York, London and San Francisco, (1976)) it is necessary to know beforehand the protein 3D structure (or at least the protein structure factors).

The provision of the pharmacophore of the invention will also allow the development of compounds which interact with the binding pocket regions of FGFR (for example to act as inhibitors of a FGFR1, 2, or 3, or 4) based on a fragment linking or fragment growing approaches.

For example, pharmacophore of Formula I herein can provide a starting point for medicinal chemistry to optimize the interactions using a structure-based approach. The fragments can be combined onto a template e.g. the pharmacophore of Formula I or pharmacophore of Formula I could be used as the starting point for 'growing out' an inhibitor into other pockets of the protein (Blundell T L, Jhoti H, Abell C, Nature Reviews Drug Discovery, 1, 45-54, 2002, Carr, R; Jhoti, H; Drug Discov. Today, 2002, 7(9), 522-527). The fragments can be positioned in the binding pockets of FGFR and then 'grown' to fill the space available, exploring the electrostatic, van der Waals or hydrogen-bonding interactions that are involved in molecular recognition. The potency of the original weakly binding fragment thus can be rapidly improved using iterative structure-based chemical synthesis.

At one or more stages in the fragment growing approach, the compound may be synthesized and tested in a biological system for its activity. This can be used to guide the further growing out of the fragment.

Where two fragment-binding regions are identified, a linked fragment approach may be based upon attempting to link the two fragments directly, or growing one or both fragments in the manner described above in order to obtain a larger, linked structure, which may have the desired properties.

E. Uses of the Pharmacophore of the Invention in In Silico Analysis and Design

Current computational techniques provide a powerful alternative to the need to generate crystals and generate and analyse diffraction data. Accordingly, a particularly preferred aspect of the invention relates to in silico methods directed to the analysis and development of compounds, containing the pharmacophoric feature of the present invention, or derived or designed from the molecular fragments herein.

The approaches to structure-based drug design described below all require initial identification of possible compounds for interaction with the target bio-molecule (in this case FGFR or VEGFR2). Sometimes these compounds are known e.g. from the research literature. However, when they are not, or when novel compounds are wanted, a first stage of the drug design program may involve computer-based in silico screening of compound databases (such as the Cambridge Structural Database or the Available Chemical Directory (ACD) (MDL Information Systems, San Leandro, Calif., USA) with the aim of identifying compounds which interact with the binding site or sites of the target bio-molecule. Screening selection criteria may be based on pharmacokinetic properties such as metabolic stability and toxicity or the pharmacophore of the invention. The pharmacophore can thus be used as selection criteria or filter for database screening.

Thus as a result of the determination of the FGFR selectivity pharmacophore more purely computational techniques for rational drug design may also be used to design FGFR selective inhibitors (for an overview of these techniques see e.g. Walters et al, *Drug Discovery Today*, Vol. 3, No. 4, (1998), 160-178; Abagyan, R.; Totrov, M. *Curr. Opin. Chem. Biol.* 2001, 5, 375-382). For example, automated ligand-receptor docking programs (discussed e.g. by Jones et al. in *Current Opinion in Biotechnology*, Vol. 6, (1995), 652-656 and Halperin, I.; Ma, B.; Wolfson, H.; Nussinov, R. *Proteins* 2002, 47, 409-443), can be used to design potential FGFR inhibitors on the basis of the pharmacophore of the invention, which have reduce affinity for or activity against VEGFR.

The determination of the pharmacophore for FGFR selective inhibitors provides a basis for the design of new and specific ligands for FGFR. For example, computer modelling programs may be used to design different molecules expected to interact with binding cavities or other structural or functional features of FGFR. Examples of this are discussed in Schneider, G.; Bohm, H. J. *Drug Discov. Today* 2002, 7, 64-70.

More specifically, the interaction of a compound with FGFR and/or VEGFR2 can be examined through the use of computer modelling using a docking program such as GOLD (Jones et al., *J. Mol. Biol.*, 245, 43-53 (1995), Jones et al., *J. Mol. Biol.*, 267, 727-748 (1997)), GRAMM (Vakser, I. A., *Proteins*, Suppl., 1:226-230 (1997)), DOCK (Kuntz et al, *J. Mol. Biol.* 1982, 161, 269-288, Makino et al, *J. Comput. Chem.* 1997, 18, 1812-1825), AUTODOCK (Goodsell et al, *Proteins* 1990, 8, 195-202, Morris et al, *J. Comput. Chem.* 1998, 19, 1639-1662.), FlexX, (Rarey et al, *J. Mol. Biol.* 1996, 261, 470-489) or ICM (Abagyan et al, *J. Comput. Chem.* 1994, 15, 488-506). This procedure can include computer fitting of compounds to FGFR or VEGFR2 to ascertain how well the shape and the chemical structure of the compound will bind to FGFR and/or VEGFR2. In addition the availability of pharmacophore of Formula I will allow the generation of highly predictive pharmacophore models for virtual library screening or compound design.

Also, computer-assisted, manual examination of the binding site structure of FGFR or VEGFR2 may be performed. The use of programs such as GRID (Goodford, *J. Med. Chem.*, 28, (1985), 849-857)—a program that determines probable interaction sites between molecules with various functional groups and an enzyme surface—may also be used to analyse the binding cavity or cavities to predict partial structures of inhibiting compounds.

Computer programs (e.g. molecular simulation methods such as Tounge and Reynolds, *J. Med. Chem.*, 46, (2003), 2074-2082) can be employed to estimate the attraction, repulsion, and steric hindrance of the two binding partners (i.e. the tyrosine kinase e.g. FGFR or VEGFR2 and a candidate modulator). Generally the tighter the fit, the fewer the steric hindrances, and the greater the attractive forces, the more potent the potential modulator since these properties are consistent with a tighter binding constant. Furthermore, the more specificity in the design of a potential drug, the more likely it is that the drug will not interact with other proteins as well. This will tend to minimise potential side-effects due to unwanted interactions with other proteins.

A plurality (for example two, three or four) of (typically spaced) FGFR or VEGFR2 binding sites may be characterised and a plurality of respective compounds designed or selected. The candidate modulator may then be formed by linking the respective compounds into a larger candidate modulator which preferably maintains the relative positions and orientations of the respective compounds at the binding sites. The larger candidate modulator may be formed as a real molecule or by computer modelling.

In one embodiment a plurality of candidate agent compounds are screened or interrogated for interaction with the binding sites. In one example, this involves providing the structures of the candidate agent compounds, each of which is then fitted to computationally screen a database of compounds (such as the Cambridge Structural Database or ACD) for interaction with the binding sites, i.e. the candidate agent compound may be selected by computationally screening a database of compounds for interaction with the binding sites and containing the pharmacophore of the invention (see Martin, *J. Med. Chem.*, vol 35, 2145-2154 (1992)). In another example, a 3-D descriptor for the agent compound is derived where the descriptor includes the pharmacophoric feature(s) of the invention. The descriptor may then be used to interrogate the compound database, the identified agent compound being the compound which matches with the features of the descriptor.

Detailed information either structural or activity data can be obtained about the binding of the compound to FGFR and/or VEGFR2, and in the light of this information adjustments can be made to the structure or functionality of the compound, e.g. to improve its interaction with FGFR. The above steps may be repeated and re-repeated as necessary.

F. Uses of Crystallographic, NMR, ITC, Thermal denaturation, Mass Spectrometry and SPR Assays X-ray crystallography, NMR spectroscopy, ITC, thermal denaturation, mass spectrometry and Surface Plasmon Resonance (SPR) assays may be used in several ways for drug design. The pharmacophore of the invention is particularly suitable for the design, screening, development and optimization of modulators of FGFR which have greater affinity for FGFR than VEGFR2. It is a preferred aspect of the invention that modulators are inhibitors, in particular inhibitors of FGFR1, 2, 3 or 4 most preferably inhibitors of FGFR1, 2, or 3.

By using the methods discussed below the candidate modulators can be identified as binding to FGFR in particular binding to FGFR with greater affinity than to VEGFR2.

A) X-ray Crystallography

Complexes of FGFR or VEGFR2 and compound can be crystallized and analyzed using X-ray diffraction methods, e.g. according to the approach described by Greer et al., *J. of Medicinal Chemistry*, Vol. 37, (1994), 1035-1054, and difference Fourier electron density maps can be calculated based on X-ray diffraction patterns of soaked crystals of FGFR in particular FGFR1 or 2, or VEGFR2 or co-crystallized FGFR in particular FGFR1 or 2, or VEGFR2 and the solved structure of uncomplexed FGFR in particular FGFR1 or 2, or VEGFR2. These maps can then be analyzed e.g. to determine whether and where a particular compound binds to the FGFR1 or 2 and/or changes the conformation of FGFR1 or 2.

Electron density maps can be calculated using programs such as those from the CCP4 computing package (Collaborative Computational Project 4. The CCP4 Suite: Programs for Protein Crystallography, *Acta Crystallographica, D*50, (1994), 760-763.). For map visualization and model building programs such as "O" (Jones et al., *Acta Crystallographica*, A47, (1991), 110-119) or "QUANTA" (1994, San Diego, Calif.: Molecular Simulations) can be used.

The crystal structures of a series of complexes may then be solved by molecular replacement and compared with that of FGFR or VEGFR2 in the PDB file. Potential sites for modification within the various binding sites of the enzyme may thus be identified. This information provides an additional tool for determining the most efficient binding interactions, for example, increased hydrophobic interactions, between FGFR or VEGFR2 and the candidate modulator.

All of the complexes referred to above may be studied using well-known X-ray diffraction techniques and may be refined against 1.5 to 3.5 Å resolution X-ray data to an R value of about 0.30 or less using computer software, such as CNX (Brunger et al., *Current Opinion in Structural Biology*, Vol. 8, Issue 5, October 1998, 606-611, and commercially available from Accelerys, San Diego, Calif.), X-PLOR (Yale University, ©1992, distributed by Accelerys), as described by Blundell et al, (1976) and Methods in Enzymology, vol. 114 & 115, H. W. Wyckoff et al., eds., Academic Press (1985).

This information may thus be used to optimize known classes of FGFR substrates or inhibitors, and more importantly, to design and synthesize novel classes of FGFR selective modulators, preferably FGFR selective inhibitors.

Analysing the complex by X-ray crystallography will determine the ability of the candidate compound to interact with FGFR or VEGFR2. Analysis of the co-complexes of the tyrosine kinase may involve e.g. phasing, molecular replacement or calculating a Fourier difference map of the complex as discussed above.

Thus, in a further aspect, the invention provides a method for determining the structure of a compound bound to the FGFR and/or VEGFR2, said method comprising: (a) providing a crystal of the FGFR and/or VEGFR2 according to the invention; (b) soaking the crystal with said compounds; and (c) determining the structure of said tyrosine kinase-compound complex.

Alternatively, the tyrosine kinase and compound may be co-crystallized. Thus the invention provides a method for determining the structure of a compound bound to FGFR and/or VEGFR2, said method comprising; mixing the protein with the compound(s), crystallizing the protein-compound(s) complex; and determining the structure of said tyrosine kinase-compound(s) complex.

A mixture of compounds may be soaked or co-crystallized with the crystal, wherein only one or some of the compounds may be expected to bind to FGFR or VEGFR2. As well as the structure of the complex, the identity of the complexing compound(s) is/are then determined.

In either case, substrate or a substrate analogue thereof may optionally be present.

The analysis of such structures may employ (i) X-ray crystallographic diffraction data from the complex and (ii) a three-dimensional structure of FGFR or VEGFR2, or at least selected coordinates thereof, to generate a difference Fourier electron density map of the complex. The difference Fourier electron density map may then be analysed, to identify the binding mode of the modulator.

B) NMR Spectroscopy

NMR spectroscopy allows for the detection of interactions between ligands and a given target protein.

This technique may be applied to detect binding, by either observing the spectrum of the recombinant protein, or that of the binding ligand (Lepre, Moore & Peng, Chem. Rev. 2004, 104, 3641). The former methods are currently limited by the size of the protein, and include the so-called 'SAR by NMR' method of Shuker et al (Science 274, 1531-1534 (1996)). The kinase domain described here are within the permitted size range for this technique, and thus this invention enables identification of binding compounds that could be optimised into modulators of FGFR or VEGFR2 activity. Methods that observe changes in the NMR properties of the ligand are not limited by the size of the protein, and again could be applied to the compounds of this invention. These include NMR methods that detect changes in ligand relaxation rates (T1 and T2/T1ρ) and cross-relaxation rates, either ligand-to-ligand (NOE), protein-to-ligand (trNOE and STD-NMR) or water-to-ligand (water-LOGSY) rates, on introduction of the target protein.

The WaterLOGSY experiment (Dalvit et al., J. Biomol. NMR, 118, 2000) is particularly well suited for finding compounds that bind with affinities that are generally too weak (in the 10 M to 10 mM range) to be detected by more conventional binding assays. The WaterLOGSY experiment is NOE based, with a long mixing period (ca 1.5 sec) during which magnetization can be transferred from the protein to a binding ligand. In the absence of protein or when a compound is not interacting with the protein, no magnetization can be transferred from the protein to the compound, and the rapid tumbling of the compound results in positive NOEs and negative compound signals in the NMR spectrum. On the other hand, if a compound is binding to the protein, magnetization is transferred from the protein to the compound which, due to the slow tumbling of the protein, results in negative NOEs and positive compound signals. Interfering protein signals are not observed in the experiment, due to a large excess of compound and the suppression of protein signals. Medium throughput can be achieved by analysing mixtures of compounds. In order to identify the individual compound signals in a mixture, a reference spectrum is recorded for each compound, which can then be compared to the WaterLOGSY spectrum of the mixture. In addition, active site directed binding of a compound can be confirmed by carrying out a competition experiment with a high affinity ligand that is known to bind in the active site. Compounds binding in the active site will be displaced by the high affinity ligand, resulting in a change from positive to negative compound signals. The signals of compounds binding elsewhere on the protein or non-specifically will remain positive even in the presence of the high affinity ligand.

A typical experiment can be conducted using a 500-1000 MHz spectrometer. For each tyrosine kinase/compound mixture a 1D reference spectrum and a WaterLOGSY spectrum is recorded. The mixtures typically contained 4-6 compounds, each at a concentration of 100-300 µM. Competition experiments are performed by adding a high affinity compound to the tyrosine kinase/compound mixture. The WaterLOGSY spectra of tyrosine kinase/compound mixtures in the absence and presence of the high affinity ligand are compared. A compound can be deemed an active site binder only if it could be displaced by the high affinity ligand. For each active site binder observed in a mixture, the experiment is normally repeated with the individual compound to confirm the observation.

Thus, the method of the invention may comprise the further steps of: (a) obtaining or synthesising said candidate modulator; (b) forming a complex of the tyrosine kinase and said candidate modulator; and (c) analysing said complex by X-ray crystallography or NMR spectroscopy to determine the ability of said candidate modulator to interact with the tyrosine kinase.

C) Surface Plasmon Resonance (SPR)

Surface plasmon resonance (SPR) methods that could be used in ligand identification include those methods where a protein target is immobilised on the surface of the chip and candidate ligands passed over the protein in the mobile phase (Karlsson, R., Anal. Biochem., 1994, 221, 142-151; Karlsson, R., Kullman-Magnusson, M., Hamalainen, M.-D., Remaeus, A., Andersson, K., Borg, P., Gyzander, E., Deinum, J.; Analytical Biochemistry, 2000; 278, 1-13). Measurement of association and dissociation of the ligand at a range of ligand concentrations allows calculation of ligand binding affinities (reviewed in Rich & Myszka, Curr Opin Biotechnol. 11, 54-61 (2000)).

Commercial realisations of SPR allows for the detection of interactions between ligand and target protein in real time. Monitoring of protein/ligand interactions is done with an optical detection system based on Surface Plasmon Resonance (SPR). In order to measure the interaction between ligand and protein one of the components must be covalently attached to the surface of a sensor chip. This chip is composed of a glass slide with a thin layer of gold deposited on one side and a matrix such as dextran covering the gold surface. The phenomenon of SPR occurs when light is reflected from a conducting film that is sandwiched between two non-absorbing media. The conducting film is the gold layer of the chip and the two media of different refractive index are the glass slide and the aqueous sample flowing over the surface of the chip. Surface plasmon resonance causes a decrease in intensity of the reflected light at a specific angle. The angle at which the decrease occurs is sensitive to the mass of solutes at the surface of the chip. When molecules bind to the surface of the chip the mass increases affecting the angle at which the decrease in intensity occurs. For example, a ligand attached to the chip surface would bind the target protein and increase the mass at the chip surface.

In a typical experiment, a tyrosine kinase can be assayed by attaching a high affinity binder to the surface of a sensor chip The presence of a tyrosine kinase inhibitor reduces the signal by binding to the tyrosine kinase and inhibiting the interaction with the high affinity binder on the chip. A tyrosine kinase inhibitor can thus be detected.

Thus, the method of the invention may comprise the further steps of: (a) obtaining or synthesising said candidate modulator; (b) forming a complex of tyrosine kinase e.g. FGFR or VEGFR2 and said candidate modulator; and (c) analysing said complex by SPR assay to determine the ability of said candidate modulator to interact with FGFR or VEGFR2.

D) Biological Assay

Having obtained and characterized a modulator compound according to the invention, the invention further provides a method for determining the activity of candidate modulator against FGFR and/or VEGFR2 which method comprises: (a) providing the tyrosine kinase e.g. FGFR or BEGFR2 under conditions where, in the absence of modulator, the tyrosine kinase is able to synthesize product; (b) providing a modulator compound; and (c) determining the extent to which the activity of the tyrosine kinase is altered by the presence of said compound.

The invention further provides a method determining the activity of candidate modulator against FGFR and/or VEGFR2 which method comprises: (a) providing FGFR or VEGFR2 under conditions where, in the absence of candidate modulator, the FGFR or VEGFR2 is able to synthesize ADP from ATP; (b) providing a candidate modulator; and (c) determining the extent to which the activity of FGFR or VEGFR2 is altered by the presence of said candidate modulator.

In addition a number of cell assays could be used to assess the reduced activity of VEGFR compared to FGFR for example cell based assays using as cell lines such as JIM, or HUVEC.

In addition a number of biological models could be used to assess the reduced activity of the compounds for VEGFR compared to FGFR. A number of animal models exist to measure the potential hypertensive effects of small molecule inhibitors. They can be classified into two main types; indirect and direct measurements. The most common indirect method is the cuff technique. Such methods have the advantages of being non-invasive and as such can be applied to a larger group of experimental animals however the process allows only intermittent sampling of blood pressure and requires the animal to be restrained in some way. Application of restraint can stress the animal and means that changes in blood pressure attributable to a specific drug effect can be hard to pick up.

Direct methodologies include those that make use of radio telemetry technology or via indwelling catheters connected to externally mounted transducers. Such methods require a high level of technical expertise for the initial surgery involved in implantation and costs involved are high. However a key advantage is that they allow continuous monitoring of blood pressure without restraint over the time period of the experiment. These methods are reviewed in Kurz et. al, Hypertension. 2005 45: 299-310.

Thus, the method of the invention may comprise the further steps of: (a) obtaining or synthesising said candidate modulator; (b) put the candidate modulator into an animal model of hypertension; and (c) measure the potential hypertensive effects of candidate modulator.

E) ITC and Thermal Denaturation

Isothermal titration calorimetry (ITC) may be used as an alternative method to detect the interaction between compounds and a target protein. Again various methods have been described, including direct titration of a protein solution with the ligand of interest and measurement of the associated enthalpy changes (reviewed in Leavitt & Friere, Curr. Opin. Struct. Biol. 11, 560-566 (2001)), low c-value methods for weak-binding ligands (Turnbull & Daranas, J Am Chem Soc. 125, 14859-66 (2003)), and competition methods for weak-binding ligands (Zhang & Zhang, Curr Opin Biotechnol. 11, 54-61 (2000)) and extremely tight-binding ligands (Velazquez-Campoy, A., Kiso, Y., Freire, E. Arch. Biochem. Biophys. 390, 169-175 (2001).

In addition to ITC, differential scanning calorimetry (DSC) is another calorimetric method that can be used to identify protein ligands. This DSC method measures the effect of ligands upon the thermal denaturation mid-point of a target protein (Plotinov et al, Assay & Drug Development Technologies 1, 83-89 (2002)). Thermal denaturation methods take advantage of the observed energetic coupling between protein stability and ligand binding, thus allowing identification of ligands through their ability to stabilise the protein. This effect can be measured in several other ways, for example by using a fluorescent reporter dye to measure changes in the temperature at which thermal denaturation occurs (Pantoliano et al, J. Biomol. Screening 6, 429-440 (2001)) or by using a fluorescent reporter dye to measure the ability of candidate ligands to alter the rate at which thermal denaturation occurs (Epps et al, Anal. Biochem. 292, 40-50 (2001)).

Thus, the method of the invention may comprise the further steps of: (a) obtaining or synthesising said candidate modulator; (b) forming a complex of FGFR or VEGFR2 and said candidate modulator; and (c) analysing said complex by thermal denaturation or ITC to determine the ability of said candidate modulator to interact with FGFR or VEGFR.

F) Mass Spectrometry

There are three mass spectrometry methods that have been used to detect ligand binding to proteins. In the first method, the protein is exposed to a mixture of ligands in solution. Protein-ligand complexes are then separated from unbound ligands by a chromatographic method and the ligands identified by mass spectrometry after dissociation of the complex (F J Moy, K Haraki, D Mobilio, G Walker, R Powers, K Tabei, H Tong, M M Siegel, Anal Chem 2001, 73, 571-581). In a second method, the protein is exposed to single ligand or a mixture of ligands in solution. Protein-ligand complexes are detected directly by obtaining mass spectra of the complex under conditions where association of the ligand is maintained in the mass spectrometer and the identity of the ligand is determined by analysis of the mass of the complex (E E Swayze, E A Jefferson, K A Sannes-Lowery, L B Blyn, L M Risen, S Arakawa, S A Osgood, S A Hofstadtler and R H Griffey, J. Med. Chem. 2002, 45, 3816-3819). In a third method, ligand binding to the protein is detected via a change in the rate of hydrogen-deuterium exchange when the protein is exposed to deuterated solvents in the presence and absence of a ligand. Various experimental schemes are possible which measure global or local changes in exchange caused by the presence of a ligand (K D Powell, S Ghaemmaghami, M Z Wang, L Ma, T G Oas and M C Fitzgerald JACS 2002, 124, 10256-10257; M M Zhu, D L Rempel, Z Du, M L Gross, JACS 2003, 125, 5253-5253).

Thus, the method of the invention may comprise the further steps of: (a) obtaining or synthesising said candidate modulator; (b) forming a complex of FGFR or VEGFR2 and said candidate modulator; and (c) analysing said complex by mass spectrometry to determine the ability of said candidate modulator to interact with FGFR or VEGFR.

G. Compounds of the Invention

Having designed or selected possible binding candidate modulators (e.g. by in silico analysis, "wet" chemical methods, X-ray analysis etc.) by determining those which have favourable fitting properties (e.g. strong attraction between candidate and FGFR), these can then be screened for activity.

Consequently all the methods of compound design and identification outlined above can optionally include the step of: (a) obtaining or synthesising the candidate modulator; and (b) contacting the candidate modulator with FGFR to determine the ability of the candidate modulator to interact with FGFR.

In some instances, in the latter step the candidate modulator is contacted with FGFR under conditions to determine its function e.g. its ability to bind to FGFR and/or to modulate (e.g. inhibit) FGFR activity.

For example, in the contacting step above the candidate modulator is contacted with FGFR in the presence of a substrate, and typically a buffer, to determine the ability of said candidate modulator to inhibit FGFR. For example, an assay mixture for FGFR may be produced which comprises the candidate modulator, substrate e.g. ATP and buffer.

Detailed structural information can be obtained about the binding of the candidate modulator to FGFR or VEGFR, and in the light of this information adjustments can be made to the structure or functionality of the candidate modulator, e.g. to improve binding to the FGFR binding cavity or cavities or to decrease binding to the VEGFR binding cavity or cavities. The above steps may be repeated and re-repeated as necessary.

The various functional groups and substituents making up the compounds of the invention are typically chosen such that the molecular weight of the compound does not exceed 1000 daltons. More usually, the molecular weight of the compound will be less than 750, for example less than 700, or less than 650, or less than 600, or less than 550 daltons. More preferably, the molecular weight is less than 525 and, for example, is 500 daltons or less. Most preferably, the molecular weight is less than 450 daltons.

Following identification of such compounds, it may be manufactured and/or used in the preparation, i.e. manufacture or formulation, of a composition such as a medicament, pharmaceutical composition or drug. These may be administered to individuals.

Thus, the present invention extends in various aspects not only to a compound as provided by the invention, but also a pharmaceutical composition, medicament, drug or other composition comprising such a compound e.g. for treatment (which may include preventative treatment) of disease; a method comprising administration of such a composition to a patient, e.g. for treatment of disease; use of such an inhibitor in the manufacture of a composition for administration, e.g.

for treatment of disease; and a method of making a pharmaceutical composition comprising admixing such an inhibitor with a pharmaceutically acceptable excipient, vehicle or carrier, and optionally other ingredients.

Thus a further aspect of the present invention provides a method for preparing a medicament, pharmaceutical composition or drug, the method comprising:
(a) identifying FGFR candidate modulator (which may thus be termed a lead compound) by a method of any one of the other aspects of the invention disclosed herein; (b) optimising the structure of the candidate modulator; and (c) preparing a medicament, pharmaceutical composition or drug containing the optimised candidate modulator. The above-described processes of the invention may be iterated in that the modified compound may itself be the basis for further compound design. Detailed structural information can be obtained about the binding of the candidate modulator to FGFR, and in the light of this information adjustments can be made to the structure or functionality of the candidate modulator, e.g. to improve binding to the binding cavity or cavities. The above steps may be repeated and re-repeated as necessary.

Modification will be those conventional in the art known to the skilled medicinal chemist, and will include, for example, substitutions or removal of groups containing residues which interact with the amino acid side chain groups of FGFR structures. For example, the replacements may include the addition or removal of groups in order to decrease or increase the charge of a group in a test compound, the replacement of a charged group with a group of the opposite charge, or the replacement of a hydrophobic group with a hydrophilic group or vice versa. It will be understood that these are only examples of the type of substitutions considered by medicinal chemists in the development of new pharmaceutical compounds and other modifications may be made, depending upon the nature of the starting compound and its activity.

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions. The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump. Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

Liposomes are closed spherical vesicles composed of outer lipid bilayer membranes and an inner aqueous core and with an overall diameter of <100 µm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms. Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here. Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect. Compositions may be used, e.g. for treatment (which may include preventative treatment) of a disease such as multiple myeloma. Thus the invention provides a method comprising administration of such a composition to a patient, e.g. for treatment of a disease such as multiple myeloma; use of such an agent compound in the manufacture of a composition for administration, e.g. for treatment of a disease such as multiple myeloma; and a method of making a pharmaceutical composition comprising admixing such an agent compound with a pharmaceutically acceptable excipient, vehicle or carrier, and optionally other ingredients.

The term "treatment" as used herein in the context of treating a disease or condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the disease or condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously.

The compounds of the invention may be derivatised in various ways. As used herein "derivatives" of the compounds includes salts (e.g. pharmaceutically acceptable salts), any complexes (e.g. inclusion complexes or clathrates with compounds such as cyclodextrins, or coordination complexes with metal ions such as $Mn^{2+}$ and $Zn^{2+}$), esters such as in vivo hydrolysable esters, free acids or bases, polymorphic forms of the compounds, solvates (e.g. hydrates), prodrugs or lipids, coupling partners and protecting groups. By "prodrugs" is meant for example any compound that is converted in vivo into a biologically active compound. Unless otherwise specified, a reference to a particular compound also includes ionic, salt, solvate, and protected forms of thereof, for example, as discussed herein.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids. The compounds of the invention may exist as mono- or di-salts depending upon the pKa of the acid from which the salt is formed.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

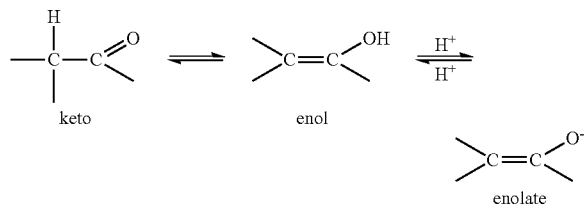

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry by Jerry March*, 4$^{th}$ Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is:

$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

H. Biological Activity

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

Thus, for example, it is envisaged that the compounds of the invention will be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3.

Preferred compounds are compounds that inhibit one or more FGFR selected from FGFR1, FGFR2 and FGFR3, and also FGFR4. Preferred compounds of the invention are those having $IC_{50}$ values of less than 0.1 µM.

Compounds of the invention also have activity against VEGFR.

Compounds of the invention also have activity against PDGFR kinases. In particular, the compounds are inhibitors of PDGFR and, for example, inhibit PDGFR A and/or PDGFR B.

In addition many of the compounds of the invention exhibit selectivity for the FGFR 1, 2, and/or 3 kinase, and/or FGFR4 compared to VEGFR (in particular VEGFR2) and/or PDGFR and such compounds represent one preferred embodiment of the invention. In particular, the compounds exhibit selectivity for VEGFR2. For example, many compounds of the invention have $IC_{50}$ values against FGFR1, 2 and/or 3 and/or FGFR4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, VEGFR and/or PDGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the iso forms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the iso forms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis.

Thus, in the pharmaceutical compositions, uses or methods of this invention for treating a disease or condition comprising abnormal cell growth, the disease or condition comprising abnormal cell growth in one embodiment is a cancer.

Further T-cell lymphoproliferative diseases include those derived from natural Killer cells. The term B-cell lymphoma includes diffuse large B-cell lymphoma.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

A further example of a tumour of mesenchymal origin is Ewing's sarcoma.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

A yet further subset of cancers includes multiple myeloma, bladder and cervical carcinomas.

It is further envisaged that the compound of the invention having FGFR such as FGFR1 inhibitory activity, will be particularly useful in the treatment or prevention of breast cancer in particular Classic Lobular Carcinomas (CLC).

As the compounds of the invention have FGFR4 activity they will also be useful in the treatment of prostate or pituitary cancers.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are in the treatment of multiple myeloma (in particular multiple myeloma with t(4;14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful for the treatment of lobular carcinomas such as CLC (Classic lobular carcinoma).

As the compounds have activity against FGFR3 they will be useful in the treatment of multiple myeloma and bladder.

In particular the compounds are useful for the treatment of t(4;14) translocation positive multiple myeloma.

As the compounds have activity against FGFR2 they will be useful in the treatment of endometrial, ovarian, gastric and colorectal cancers. FGFR2 is also overexpressed in epithelial ovarian cancer, therefore the compounds of the invention may be specifically useful in treating ovarian cancer such as epithelial ovarian cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR, VEGFR or PDGFR signalling may be determined by a method as set out in the section headed "Methods of Diagnosis".

It is further envisaged that the compounds of the invention, and in particular those compounds having FGFR, VEGFR or PDGFR inhibitory activity, will be particularly useful in the treatment or prevention of cancers of a type associated with or characterised by the presence of elevated levels of FGFR, VEGFR or PDGFR, for example the cancers referred to in this context in the introductory section of this application.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

It is also envisaged that the compounds of the invention will be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of inflammatory diseases, cardiovascular diseases and wound healing.

FGFR, VEGFR and PDGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

It is further envisaged that the compound of the invention having FGFR such as FGFR2 or FGFR3 inhibitory activity, will be particularly useful in the treatment or prevention of the skeletal diseases. Particular skeletal diseases are achondroplasia or thanatophoric dwarfism (also known as thanatophoric dysplasia).

It is further envisaged that the compound of the invention having FGFR such as FGFR1, FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

Since compounds of the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme (Carter et al (2005), PNAS, 102(31), 11011-110116).

There are mutations that have been observed in PDGFR in imatinib-treated patients, in particular the T674I mutation. The clinical importance of these mutations may grow considerably, as to date it appears to represent the primary mechanism of resistance to src/Abl inhibitors in patients.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR or PDGFR including PDGFR-beta and PDGFR-alpha in particular the T674I mutation of PDGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

I. Methods of Treatment

It is envisaged that the compounds of the formula (I) and sub-groups thereof as defined herein will be useful in the prophylaxis or treatment of a range of disease states or conditions mediated by FGFR. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

- Topoisomerase I inhibitors
- Antimetabolites
- Tubulin targeting agents
- DNA binder and topoisomerase II inhibitors
- Alkylating Agents
- Monoclonal Antibodies.
- Anti-Hormones
- Signal Transduction Inhibitors
- Proteasome Inhibitors
- DNA methyl transferases
- Cytokines and retinoids
- Chromatin targeted therapies
- Radiotherapy, and,
- Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

K. Methods of Diagnosis

Prior to administration of a compound of the formula (I), a patient may be screened to determine whether a disease or condition from which the patient is or may be suffering is one which would be susceptible to treatment with a compound having activity against FGFR, VEGFR and/or PDGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, VEGFR and/or PDGFR or to sensitisation of a pathway to normal FGFR, VEGFR and/or PDGFR activity, or to upregulation of these growth factor signalling pathways such as growth factor ligand levels or growth factor ligand activity or to upregulation of a biochemical pathway downstream of FGFR, VEGFR and/or PDGFR activation.

Examples of such abnormalities that result in activation or sensitisation of the FGFR, VEGFR and/or PDGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al. (2001), J. Bone Miner. Res., 16, 832-845). In particular activating mutations in FGFR2 have been identified in 10% of endometrial tumours (Pollock et al, Oncogene, 2007, 26, 7158-7162).

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al. (2000), Endocr. Rel. Cancer, 7, 165). A particular mutation T674I of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006), Clin Cancer Res. 12(22), 6652-6662).

Alternatively, a biological sample taken from a patient may be analysed for loss of a negative regulator or suppressor of FGFR, VEGFR or PDGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, VEGFR and/or PDGFR. The term diagnosis includes screening. By marker we include genetic markers including, for example, the measurement of DNA composition to identify mutations of FGFR, VEGFR and/or PDGFR. The term marker also includes markers which are characteristic of up regulation of FGFR, VEGFR and/or PDGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, VEGFR and/or PDGFR may mean that the patient would be particularly suitable for treatment with a FGFR, VEGFR and/or PDGFR inhibitor. Tumours may preferentially be screened for presence of a FGFR, VEGFR and/or PDGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, VEGFR and/or PDGFR, or detection of FGFR, VEGFR and/or PDGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105 (Mineo et al. (2004) J Clin Pathol. 57(6), 591-7).

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung and breast cancer.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect of the inventions includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Thus a further aspect of the invention is a method for the diagnosis and treatment of a disease state or condition mediated by a FGFR kinase, which method comprises (i) screening a patient to determine whether a disease or condition from which the patient is or may be suffering is one which would be susceptible to treatment with a compound having activity against FGFR; and (ii) where it is indicated that the disease or condition from which the patient is thus susceptible, thereafter administering to the patient a compound comprising the pharmacophore of formula 1 and sub-groups or examples thereof as defined herein.

EXEMPLIFICATION

The invention will now be described with reference to specific Examples. These are merely exemplary and for illustrative purposes only. They are not intended to be limiting in any way to the scope of the invention described.

Examples of Molecular Fragments

Procedure A

Procedure A1:
3-Imidazo[1,2-a]pyridin-3-yl-phenylamine

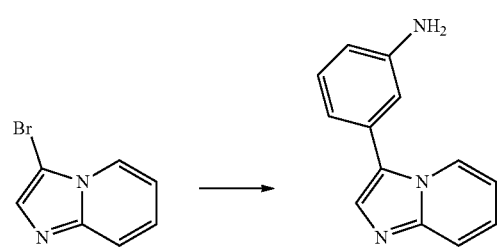

A mixture of 3-bromo-imidazo[1,2-a]pyridine (2.7 g, 13.7 mmol) and 3-aminobenzeneboronic acid (2.4 g, 17.5 mmol) in CH$_3$CN (20 ml) and 2N aqueous Na$_2$CO$_3$ (20 ml) was deoxygenated by evacuation then refill with N₂ (×3). PdCl₂dppf (500 mg, 0.68 mmol) was added and the mixture was deoxygenated again (×3). The reaction was stirred and heated at 80° C. for 8 hours. After cooling to RT the mixture was partitioned between EtOAc/H₂O and then filtered through Celite®. The Celite® was washed with CH₂Cl₂. The layers were separated and the aqueous layer was extracted with CH₂Cl₂ (×2). The combined extracts were dried (MgSO₄), filtered and evaporated. The residue was purified by chromatography on silica (100% CH₂Cl₂→2% 2M NH₃-MeOH/CH₂Cl₂) to give the title compound (1.9 g, solid). MS: [M+H]⁺ 210

Procedure A2:
N-(3-Pyrazolo[1,5-a]pyridin-3-yl-phenyl)-acetamide

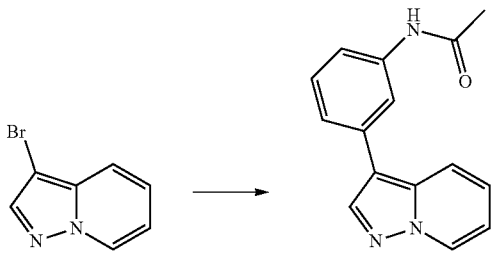

A mixture of 3-bromo-pyrazolo[1,5-a]pyridine (197 mg, 1 mmol), (3-acetylaminophenyl)boronic acid (179 mg), K₂CO₃ (6 eq) and bis(tri-t-butylphosphine)palladium (0) (5 mg) in PhMe (1 ml), MeOH (1 ml), EtOH (1 ml), and H₂O (1.8 ml) was stirred and heated at 155° C. in the microwave for 30 minutes. The mixture was partitioned between EtOAc/H₂O. The layers were separated and the organic layer was dried, filtered and evaporated. The residue was crystallised from MeOH to give the title compound (50 mg). MS: [M+H]⁺ 252

Procedure B (3-Imidazo[1,2-a]pyridin-3-yl-phenyl)-pyridin-3-yl-amine

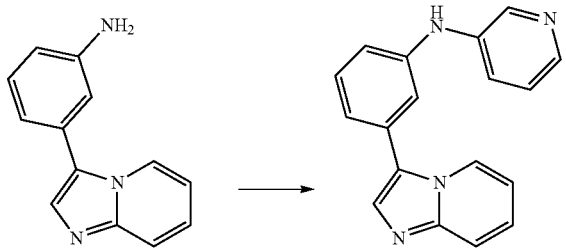

A mixture 3-imidazo[1,2-a]pyridin-3-yl-phenylamine (315 mg, 1.5 mmol), 3-bromopyridine (160 μl, 1.66 mmol), (±)-Binap (93 mg, 0.15 mmol), and NaOʹBu (440 mg, 4.6 mmol) in dry dioxane (3 ml) was deoxygenated by evacuation/refill with N₂ (×3). Pd₂dba₃ (70 mg, 0.08 mmol) was added and the mixture was deoxygenated again (×3). The reaction was stirred and heated at 100° C. for 18 hours under N₂. The mixture was partitioned between EtOAc/H₂O, then filtered. The aqueous layer was extracted with EtOAc (×2). The combined extracts were dried (MgSO₄), filtered and evaporated. The residue was purified by chromatography to give the title compound. MS: [M+H]⁺ 287

Procedure C (3-Imidazo[1,2-a]pyridine-3-yl-phenyl)-pyrimidin-2-yl amine

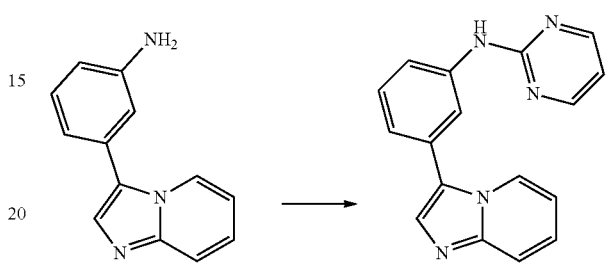

A mixture 3-imidazo[1,2-a]pyridin-3-yl-phenylamine (210 mg, 1.0 mmol), 2-chloropyrimidine (115 mg, 1 mmol) and NaOʹBu (100 mg, 1.0 mmol) in dry dioxane (2 ml) was stirred and heated at 100° C. under N₂ for 18 hours. After cooling to RT the mixture was partitioned between EtOAc/H₂O. The layers were separated and the aqueous layer was extracted with EtOAc (×2). The combined extracts were dried (MgSO₄), filtered and evaporated. The residue was purified by preparative HPLC to give the title compound (20 mg, solid). MS: [M+H]⁺ 288

Procedure D 3-(3-Imidazo[1,2-a]pyridin-3-yl-phenylamino)-thiosemicarbazide

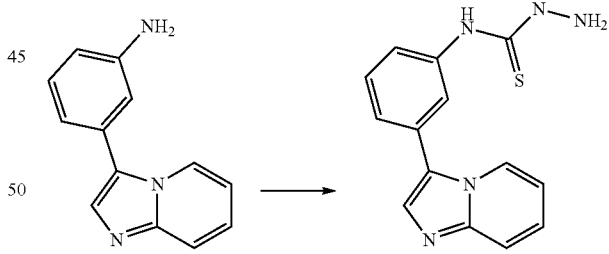

A mixture 3-imidazo[1,2-a]pyridin-3-yl-phenylamine (210 mg, 1.0 mmol) and 1,1′-thiocarbonyldi-2,2′pyridone (235 mg, 1 mmol) in dry toluene (2.5 ml) was stirred and heated at 110° C. under N₂ for 1 hour. After cooling to RT, the reaction mixture was diluted with CH₂Cl₂, washed with water (×1) and brine (×1), then dried (MgSO₄), filtered and evaporated to give the isothiocyanate.

The isothiocyanate was taken up in THF (4 ml) and cooled in an ice bath. Hydrazine hydrate (75 μl, 1.6 mmol) was added. The mixture was stirred at 0° C. for 1 hour, then the volatiles were removed in vacuo. A portion of the residue was purified by preparative HPLC to give the title compound. MS: [M+H]⁺ 284

Procedure E (3-Imidazo[1,2-a]pyridin-3-yl-phenyl)-[1,3,4]thiadiazol-2-yl-amine

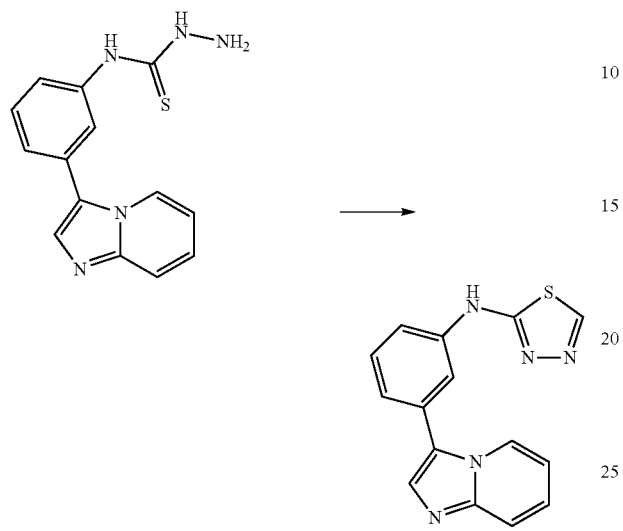

Diethyl chlorophosphate (300 µl, 2.1 mmol) was added slowly to a stirred solution of 3-(3-imidazo[1,2-a]pyridin-3-yl-phenylamino)-thiosemicarbazide (240 mg, 0.85 mmol) in dry DMF (1.5 ml) at RT under $N_2$. After 1 hour the reaction was quenched with $H_2O$ (~30 ml). The aqueous layer was extracted with EtOAc. The layers were separated and the aqueous layer was adjusted to ~pH 7 with saturated $NaHCO_3$ (aq) then extracted with $CH_2Cl_2$ (×3). The combined $CH_2Cl_2$ extracts were passed through a phase separating cartridge and then evaporated. The residue was purified by chromatography to give the title compound (30 mg, solid). MS: $[M+H]^+$ 294.

Procedure F (3-Imidazo[1,2-a]pyridin-3-yl-phenyl)-(3H-[1,2,3]triazol-4-yl)-amine

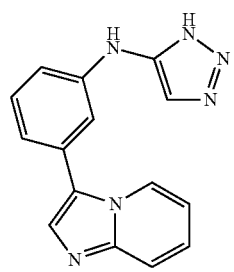

A solution of sodium nitrite (140 mg, 2 mmol) in $H_2O$ (1 ml) was added to a stirred solution of 3-imidazo[1,2-a]pyridin-3-yl-phenylamine (420 mg, 2 mmol) in 2N HCl (4 ml) such that the internal temperature <5° C. After complete addition the reaction was stirred 15 minutes at this temperature before the addition of aminoacetonitrile hydrogen sulphate (310 mg, 2 mmol) in $H_2O$ (1 ml) [internal temperature maintained <5° C.]. After 1 hour NaOAc (7 g) was added. The mixture was stirred for 1 hour with ice bath cooling, then the solid was collected by filtration. This material was taken up in EtOH directly (~10 ml). This solution was stirred and heated at 90° C. for 18 hours under $N_2$. After cooling to RT the volatiles were removed in vacuo and the residue was purified by chromatography on silica (100% $CH_2Cl_2 \rightarrow 4\%$ 2M $NH_3$-MeOH/$CH_2Cl_2$) to give the title compound (219 mg, solid). MS: $[M+H]^+$ 277

Procedure G 3-(3-Imidazo[1,2-a]pyridin-3-yl-phenylamino)-cyclopent-2-enone

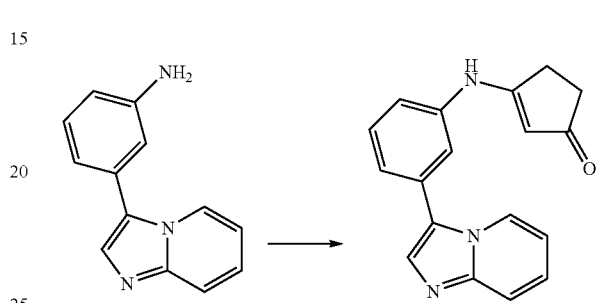

A solution of 3-imidazo[1,2-a]pyridin-3-yl-phenylamine (210 mg, 1.0 mmol), 1,3-cyclopentandione (110 mg, 1.1 mmol) and p-toluenesulfonic acid monohydrate (17 mg, 0.1 mmol) in toluene (2 ml) was stirred and heated at reflux under $N_2$ for 8 hours. After cooling to RT the mixture was diluted with methanol (~3 ml) then filtered. The solid was washed with $Et_2O$ then dried under vacuum to give the title compound. MS: $[M+H]^+$ 290.

Procedure H (3-Imidazo[1,2-a]pyridin-3-yl-phenyl)-phenyl-amine

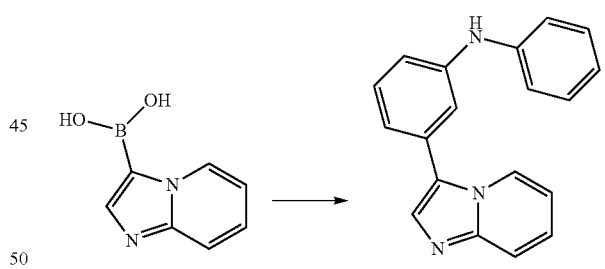

To 3-Bromodiphenylamine (0.16 g, 0.6 mmol) was added imidazo[1,2-a]pyridine-3-ylboronic acid (0.1 g, 0.6 mmol), tetrakis(triphenylphosphine)palladium (0) (35 mg, 5 mol %), EtOH (0.5 ml), toluene (0.5 ml) and 2M $Na_2CO_3$ (0.9 ml). The reaction mixture was heated at 80° C. for 6 h, before being allowed to cool and then partitioned between EtOAc and $H_2O$. The organic fraction was separated, washed with brine, dried ($MgSO_4$), filtered and the solvent removed in vacuo. The residue was purified by silica column chromatography (20%-100% EtOAc/hexane) to afford the product (4 mg). MS: $[M+H]^+$ 286.

Examples 1 to 10

By following the methods described above, the compounds of Examples 1 to 10 set out in the Table below were prepared.

| Example Number | Compound | Chemical Name | Procedure | M.S. Data [M + H]+ |
|---|---|---|---|---|
| 1 | | N-(3-Pyrazolo[1,5-a]pyridin-3-yl-phenyl)-acetamide | Procedure A2 | 252 |
| 2 | | (3-Imidazo[1,2-a]pyridin-3-yl-phenyl)-phenyl-amine | Procedure H or could be made using Procedure A1 then Procedure B using bromobenzene | 286 |
| 3 | | (3-Imidazo[1,2-a]pyridin-3-yl-phenyl)-pyridin-3-yl-amine | Procedure A1 then Procedure B | 287 |
| 4 | | (3-Imidazo[1,2-a]pyridin-3-yl-phenyl)-pyrazin-2-yl-amine | Procedure A1 then Procedure B using 2-chloropyrazine | 288 |
| 5 | | (3-Imidazo[1,2-a]pyridin-3-yl-phenyl)-thiazol-2-yl-amine | Procedure A1 then Procedure B using 2-bromothiazole | 293 |
| 6 | | (3-Imidazo[1,2-a]pyridin-3-yl-phenyl)-pyrimidin-2-yl-amine | Procedure A1 then Procedure C | 288 |

| Example Number | Compound | Chemical Name | Procedure | M.S. Data [M + H]+ |
|---|---|---|---|---|
| 7 | | 3-(3-Imidazo[1,2-a]pyridin-3-yl-phenylamino)-cyclopent-2-enone | Procedure A1 then Procedure G | 290 |
| 8 | | 3-(3-Imidazo[1,2-a]pyridin-3-yl-phenylamino)-thiosemicarbazide | Procedure A1 then Procedure D | 284 |
| 9 | | (3-Imidazo[1,2-a]pyridin-3-yl-phenyl)-[1,3,4]thiadiazol-2-yl-amine | Procedure A1, Procedure D, then Procedure E | 294 |
| 10 | | (3-Imidazo[1,2-a]pyridin-3-yl-phenyl)-(3H-[1,2,3]triazol-4-yl)-amine | Procedure A1 then Procedure F | 277 |

Example 11

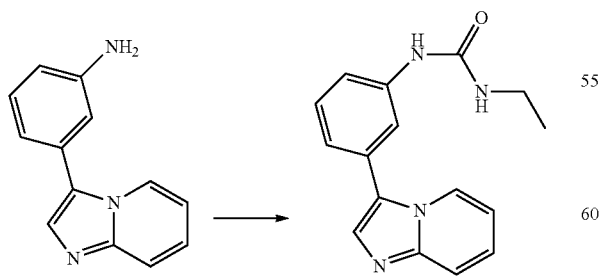

Ethyl urea analogues, such as 1-Ethyl-3-(3-imidazo[1,2-a]pyridin-3-yl-phenyl)-urea, can be synthesised from intermediate 3-Imidazo[1,2-a]pyridin-3-yl-phenyl amine from procedure A1 using ethylisocyanate with or without a base, such as triethylamine in a solvent such as dichloromethane, as described in Wynne et al. Synth Commun, 2003, 33 (6), 885-893.

Example 12

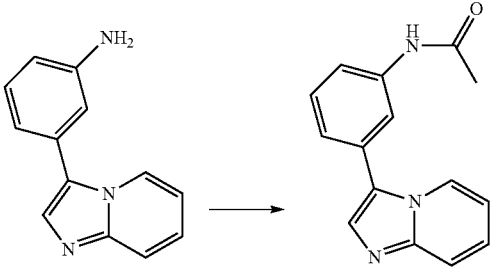

Amide analogues, such as N-(3-Imidazo[1,2-a]pyridin-3-yl-phenyl)-acetamide, can be accessed from intermediate 3-Imidazo[1,2-a]pyridin-3-yl-phenyl amine from procedure A1 using acetic acid in a solvent such as dimethylformamide with standard coupling reagents such as N-(3-dimethylaminopropyl)-N'-ethylcarbodiimide hydrochloride and 1-hydroxybenzotriazole and stirring the reaction mixture overnight at approximately 60° C. as described in Caroll et al J Heterocycl Chem 1970, 7, 297.

Example 13

Preparation of 1-(3-Imidazo[1,2-a]pyridin-3-yl-phenyl)-3-(2,2,2-trifluoro-ethyl)-urea

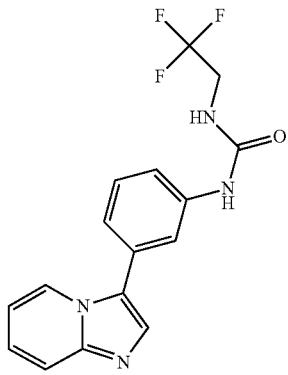

Step 1: 1-(3-Bromo-phenyl)-3-(2,2,2-trifluoro-ethyl)-urea

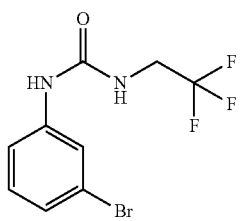

3-Bromophenyl isocyanate (1.0 ml, 8.1 mmol) was added slowly to a stirred solution of 2,2,2-trifluoroethyl amine (3.2 ml, 40 mmol) in THF (10 ml) at 0° C. under $N_2$. After 1 hour the reaction was allowed to warm to RT and kept at this temperature for 16 hours. The volatiles were removed in vacuo to give the title compound (2.5 g, solid). $^1$H NMR (400 MHz, DMSO-d6): 9.00 (1H, s), 7.86 (1H, t), 7.33 (1H, ddd), 7.26 (1H, t), 7.18 (1H, ddd), 6.89 (1H, t), 4.03-3.92 (2H, m).

Step 2: 1-[3-(4,4,5,5-Tetramethyl-[1,3,2]dioxaborolan-2-yl)-phenyl]-3-(2,2,2-trifluoro-ethyl)-urea

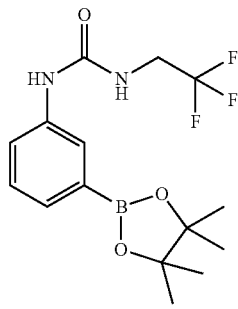

A mixture of 1-(3-bromo-phenyl)-3-(2,2,2-trifluoro-ethyl)-urea (2.1 g, 7.1 mmol), bis(pinacolato)diboron (3.6 g, 14 mmol) and KOAc (2.1 g, 21 mmol) in dry DMSO (7 ml) was deoxygenated by evacuation/refill with $N_2$ (×3). PdCl$_2$ddpf (512 mg, 0.7 mmol) was added and the mixture was deoxygenated again (×2) then stirred and heated at 100° C. under $N_2$ for 3 hours. The reaction was allowed to cool to RT and then left to stand at this temperature for 18 hours. The mixture was partitioned between EtOAc/H$_2$O then filtered through Celite®. The layers were separated and the aqueous layer was extracted with EtOAc (×1). The combined organic extracts were washed with water (×1), brine (×1), then dried (MgSO$_4$), filtered and evaporated. The residue was triturated with petrol to give the title compound (2.6 g, solid). $^1$H NMR (400 MHz, CDCl$_3$): 7.65 (1H, s), 7.60 (1H, d), 7.49 (1H, d), 7.37 (1H, t), 6.64 (1H, brs), 5.20 (1H, brs), 3.99-3.86 (2H, m), 1.35 (12H, s).

Step 3: 1-(3-Imidazo[1,2-a]pyridin-3-yl-phenyl)-3-(2,2,2-trifluoro-ethyl)-urea To a stirred solution of 3-Bromoimidazo[1,2-a]pyridine (commercially available, ex Bionet, 394 mg, 2 mmol) was added a solution of K$_3$PO$_4$ (1.27 g, 6 mmol) in H$_2$O (2 mls). 1-[3-(4,4,5,5-Tetramethyl-[1,3,2]dioxaborolan-2-yl)-phenyl]-3-(2,2,2-trifluoro-ethyl)-urea (905 mg, 2.5 mmol) dissolved in dioxane (8 ml) was added to the reaction mixture and the reaction deoxygenated by evacuation and refill of the flask with $N_2$ (×2). PdCl$_2$dppf (150 mg, 0.2 mmol) was added and the reaction mixture was deoxygenated (×3). The reaction mixture was heated at 90° C. for 16 h, cooled to RT and partitioned between CH$_2$Cl$_2$ and H$_2$O, then filtered. The layers were separated and the aqueous layer further extracted with CH$_2$Cl$_2$. The organic fractions were combined and passed through a phase separating cartridge, then the solvent removed in vacuo. The residue was purified using a SCX cartridge, washing with MeOH and eluting with 2M NH$_3$/MeOH. The resulting solid was further purified by silica column chromatography (0-3% 2M NH$_3$/MeOH in CH$_2$Cl$_2$) to afford a beige solid (335 mg). MS: [M+H]$^+$=335.

| Example Number | Compound | Chemical Name | NMR Data | M.S. Data [M + H]+ |
|---|---|---|---|---|
| 13 | 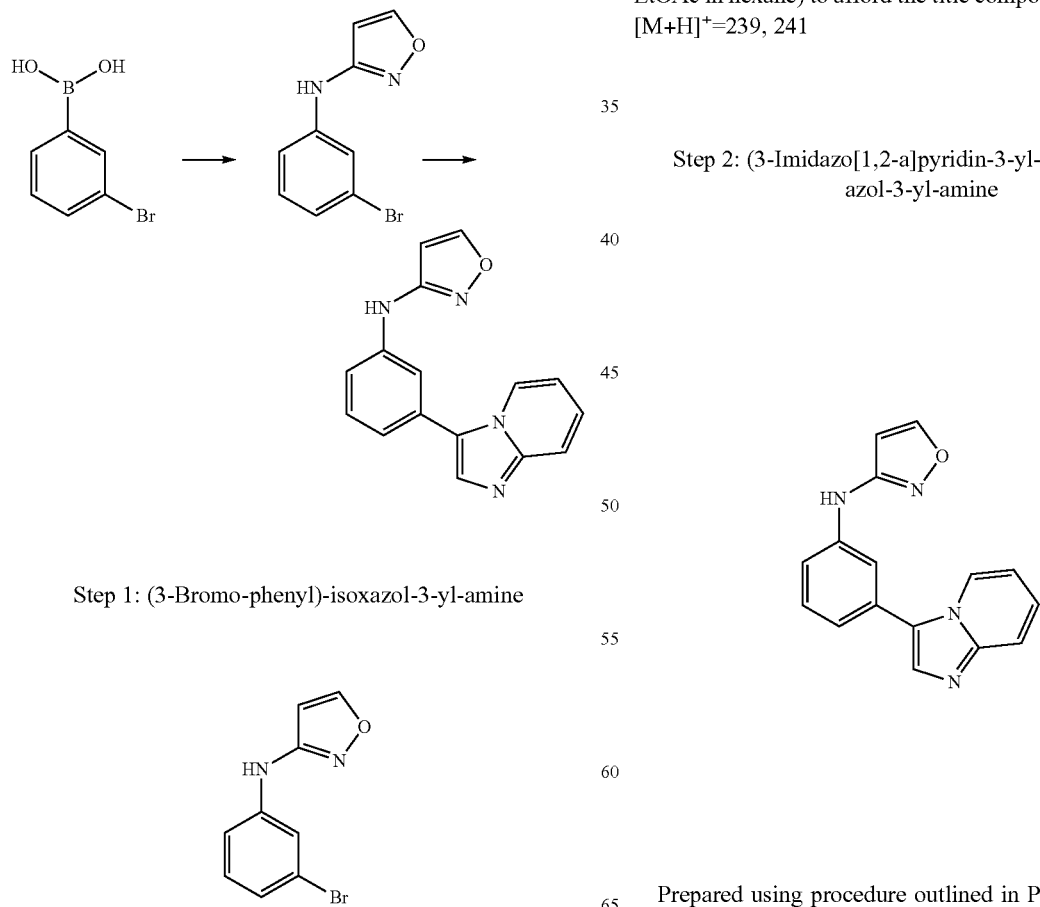 | 1-(3-Imidazo[1,2-a]pyridin-3-yl-phenyl)-3-(2,2,2-trifluoro-ethyl)-urea | 1H NMR (400 MHz, DMSO-d6): 8.94 (1 H, s), 8.56 (1 H, d), 7.74 (2 H, s), 7.66 (1 H, d), 7.48-7.41 (2 H, m), 7.31 (1 H, ddd), 7.27-7.20 (1 H, m), 6.99 (1 H, td), 6.84 (1 H, t), 4.02-3.87 (2 H, m). | [M + H] + 335.06 |

Example 14

Preparation of (3-Imidazo[1,2-a]pyridin-3-yl-phenyl)-isoxazol-3-yl-amine

Step 1: (3-Bromo-phenyl)-isoxazol-3-yl-amine

To a solution of 3-bromophenylboronic acid (2.00 g, 9.96 mmol) in CH$_2$Cl$_2$ (80 mls) was added Isoxazol-3-ylamine (0.84 g, 19.92 mmol), Cu(OAc)$_2$ (0.9 g, 0.46 mmol) and triethylamine. (14 mls). The reaction mixture was stirred at room temperature for 18 h, filtered and the resulting precipitate purified by silica column chromatography (20-80% EtOAc in hexane) to afford the title compound (0.33 g). MS: [M+H]$^+$=239, 241

Step 2: (3-Imidazo[1,2-a]pyridin-3-yl-phenyl)-isoxazol-3-yl-amine

Prepared using procedure outlined in Procedure H using (3-Bromo-phenyl)-isoxazol-3-yl-amine and imidazo[1,2-a]pyridine-3-ylboronic acid as the coupling partners.

| Example Number | Compound | Chemical Name | NMR Data | M.S. Data [M + H]+ |
|---|---|---|---|---|
| 14 | | (3-Imidazo[1,2-a]pyridin-3-yl-phenyl)-isoxazol-3-yl-amine Formate | 1 H NMR (400 MHz, Me-d3-OD): 8.63 (1 H, d), 8.37 (1 H, d), 8.25 (2 H, s), 7.84 (1 H, s), 7.77 (1 H, s), 7.68 (1 H, d), 7.55-7.40 (3 H, m), 7.25-7.15 (1 H, m), 7.07 (1 H, t), 6.19 (1 H, d). | [Molecular ion] + 277 |

Example 15

(3-Imidazo[1,2-a]pyridin-3-yl-phenyl)-(4-methoxy-phenyl)-amine

Step 1—3-(3-Chloro-phenyl)-imidazo[1,2-a]pyridine

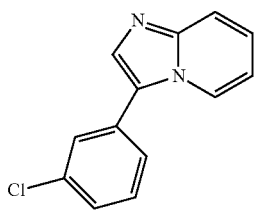

Procedure A1 using 3-chloroboronic acid

Step 2—(3-Imidazo[1,2-a]pyridin-3-yl-phenyl)-(4-methoxy-phenyl)-amine

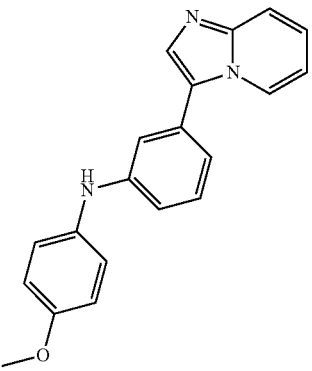

A mixture of 3-(3-Chloro-phenyl)-imidazo[1,2-a]pyridine (183 mg, 0.8 mmol), 4-Methoxy-phenylamine (200 mg, 1.6 mmol) and sodium tertbutoxide (195 mg, 2 mmol) in dry toluene (3 ml) was deoxygenated. 2'-(Dimethylamino)-2-biphenylyl-palladium(II) chloride dinorbornylphosphine complex (45 mg, 0.08 mmol) was added and the reaction mixture deoxygenated again, then heated at 110° C. for 2 h. The mixture was allowed to cool, then partitioned between $CH_2Cl_2$ and $H_2O$ and separated using a phase separating cartridge. The organic solvent was removed in vacuo and the residue purified by column chromatography, then preparative HPLC to give the desired compound (25 mg).

| Example Number | Compound | Chemical Name | NMR Data | M.S. Data [M + H]+ |
|---|---|---|---|---|
| 15 | | (3-Imidazo[1,2-a]pyridin-3-yl-phenyl)-(4-methoxy-phenyl)-amine | $^1$H NMR (400 MHz, DMSO-$d_6$): 8.54 (1 H, dt), 8.06 (1 H, s), 7.70 (1 H, s), 7.65 (1 H, dt), 7.33 (1 H, t), 7.29 (1 H, ddd), 7.17-7.07 (3 H, m), 7.03-6.94 (3 H, m), 6.94-6.85 (2 H, m), 3.73 (3H, s). | [Molecular ion] + 316 |

FGFR3 In Vitro Kinase Inhibitory Activity Assays

Enzymes (from Upstate) were prepared at 2× final concentration in 1× kinase assay buffer (as described below). Enzymes were then incubated with test compounds, biotinylated Flt3 substrate (biotin-DNEYFYV) (Cell Signalling Technology Inc.) and ATP. The reaction was allowed to proceed for 3 hours (FGFR3) at room temperature on a plate shaker at 900 rpm before being stopped with 20 µl of 35 mM EDTA, pH 8 (FGFR3). Twenty µl of 5× detection mix (50 mM HEPES pH 7.5, 0.1% BSA, 2 nM Eu-anti-pY (PY20) (PerkinElmer) 15 nM SA-XL665 (Cisbio)) was then added to each well and the plate sealed and incubated at room temperature for one hour on a plate shaker at 900 rpm. The plate was then read on a Packard Fusion plate reader in TRF mode.

| Enzyme | 1 x Assay Buffer | Flt3 substrate concentration | ATP concentration |
|---|---|---|---|
| FGFR3 | A | 0.125 µM | 8 µM |

Kinase Assay buffers were:
A: 50 mM HEPES pH 7.5, 6 mM MnCl$_2$, 1 mM DTT, 0.1% TritonX-100

VEGFR2 In Vitro Kinase Inhibitory Activity Assay

Assay reactions containing VEGFR2 enzyme (purchased from Upstate), and 250 µM Poly (Glu,Tyr) 4:1 substrate (CisBio) in 50 mM HEPES, pH 7.5, 6 mM MnCl$_2$, 1 mM DTT, 0.01% TritonX-100, 5 µM ATP (2.8 Ci/mmol) were set up in the presence of compound. Reactions were stopped after 15 minutes by adding an excess of phosphoric acid. The reaction mixture was then transferred to a Millipore MAPH filter plate where the peptide binds and the unused ATP is washed away. After washing, scintillant was added and the incorporated activity measured by scintillation counting on a Packard Topcount.

FGFR1, FGFR2, FGFR4 In Vitro Kinase Inhibitory Activity Assays

The inhibitory activity against FGFR1, FGFR2, FGFR4 can be determined at Upstate Discovery Ltd. Enzymes were prepared at 10× final concentration in enzyme buffer (20 mM MOPS, pH 7.0, 1 mM EDTA, 0.1% B-mercaptoethanol, 0.01% Brij-35, 5% glycerol, 1 mg/ml BSA). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 µl of a 3% phosphoric acid solution. Ten µl of the reaction mix was transferred to either a filtermatA or P30 filtermat and washed three times in 75 mM phosphoric acid and once in methanol before being dried for scintillation counting.

Compounds were tested at the concentrations detailed below in duplicate against all kinases and the percent activity compared to control was calculated. Where inhibition was high an IC$_{50}$ was determined.

| Enzyme | Assay Buffer | Substrate | ATP Concentration (µM) |
|---|---|---|---|
| FGFR1 | A | 250 µM KKKSPGEYVNIEFG | 200 µM |
| FGFR2 | B | 0.1 mg/ml poly(Glu, Tyr) 4:1 | 90 µM |
| FGFR4 | C | 0.1 mg/ml poly(Glu, Tyr) 4:1 | 155 µM |

Enzyme buffer A: 8 mM MOPS, pH 7.0, 0.2 mM EDTA, 10 mM MgAcetate
Enzyme buffer B: 8 mM MOPS, pH 7.0, 0.2 mM EDTA, 2.5 mM MnCl$_2$, 10 mM MgAcetate
Enzyme buffer C: 8 mM Mops, pH 7.0, 0.2 mM EDTA, 10 mM MnCl$_2$, 10 mM MgAcetate.

Cell-Based pERK ELISA Method

LP-1 or JIM-1 multiple myeloma cells were seeded in 96 well plates at 1×10$^6$ cells/ml in 200 ul per well in serum free media. HUVEC cells were seeded at 2.5×10$^5$ cells/ml and allowed to recover for 24 h prior to transfer to serum free media. Cells were incubated for 16 h at 37° C. prior to the addition of a test compound for 30 minutes. Test compounds were administered at a 0.1% final DMSO concentration. Following this 30 minute incubation a FGF-1/Heparin (FGF-1 at 100 ng/ml final and Heparin at 100 ug/ml) mixture or VEGF$^{165}$ (100 ug/ml) was added to each of the wells for a further 5 minutes. The media was removed and 50 ul ERK ELISA lysis buffer (R and D Systems DuoSet ELISA for pERK and Total ERK #DYC-1940E, DYC-1018E) added. ELISA plates and standards were prepared according to the standard DuoSet protocols and the relative amounts of pERK to total ERK in each sample calculated according to the standard curve.

HUVEC Cell Based Selectivity Assays

HUVEC cells were seeded in 6 well plates at 1×10$^6$ cells/well and allowed to recover for 24 h. They were transferred to serum free media for 16 hours prior to treatment with test compound for 30 minutes in 0.1% DMSO final. Following compound incubation FGF-1 (100 ng/ml) and Heparin (100 ug/ml) or VEGF$^{165}$ (100 ng/ml) were added for 5 minutes. Media was removed, cells washed with ice-cold PBS and lysed in 100 ul TG lysis buffer (20 mM Tris, 130 nM NaCl, 1% Triton-X-100, 10% Glycerol, protease and phosphatase inhibitors, pH 7.5). Samples containing equivalent amounts of protein were made up with LDS sample buffer and run on SDS PAGE followed by western blotting for a number of downstream VEGFR and FGFR pathway targets including phospho-FGFR3, phospho-VEGFR2 and phospho-ERK1/2.

We claim:

1. A method of identifying a compound which is a candidate modulator of fibroblast growth factor receptors (FGFR) having greater affinity for FGFR than for Vascular Endothelial Growth Factor Receptor 2 (VEGFR2), the method comprising:
    (a) designing and/or selecting a candidate modulator using the pharmacophore represented by Formula 1:

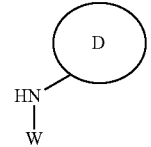

Formula 1 wherein
    Group D is a chemical group containing an unsaturated (pi) system in which at least two of the atoms in Group D form a double, triple or aromatic bond; and
    W is any atom, whether as an atom in a ring system or not;
    (b) generating on a computer a representation of said candidate modulator of step (a);

(c) generating on a computer the atomic coordinates of a FGFR protein or a portion thereof having at least the binding pocket around Asp641 (according to 1AGW numbering);
(d) fitting one or more candidate modulators according to step (b) to one or more FGFR residues to determine the probability of the candidate modulator interacting with FGFR, wherein the NH of Formula 1 forms a direct hydrogen bond with one or both of the Asp641 oxygens of the carboxylic acid;
(e) optionally modifying said candidate modulator based on the result of the fitting step;
(f) contacting said candidate modulator with FGFR and/or VEGFR2 to determine the ability of said candidate modulator to interact with FGFR and/or VEGFR2; and identifying a candidate modulator which is capable of binding or modulating FGFR, said candidate modulator having greater affinity for FGFR than for VEGFR2.

2. A method of claim 1, which further comprises
(g) identifying a candidate modulator which is capable of binding or modulating VEGFR2 to a lesser extent.

3. The method of claim 1, wherein the pharmacophore of Formula 1 is a urea, thiourea, amide, thioamide, carbamate, thiocarbamate, dithiocarbamate, amidine, guanidine, isourea, or isothiourea.

4. The method of claim 1, wherein D is a 5-membered heteroaromatic ring.

5. The method of claim 1, wherein D is of Formula 2B

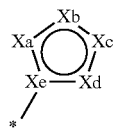

Formula 2B wherein
Xa is selected from NH, CH, and S;
Xb is selected from C, N, O, and S;
Xc is selected from N and O;
Xd is selected from C, N, O and S;
Xe is selected from C and N;
and * represents point of attachment to NH.

6. The method of claim 5, wherein Formula 2B represents a thiadiazole.

7. The method of claim 1, wherein D is of Formula 3B

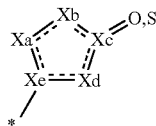

Formula 3B wherein the dotted line ---- can represent a single, or double bond;
Xa is selected from NH, CH, and S;
Xb is selected from C, N, O, and S;
Xc is selected from C, S and N;
Xd is selected from C, N, O, and S;
Xe is selected from C and N;
and * represents point of attachment to NH.

8. The method of claim 1, wherein D is of Formula 4B

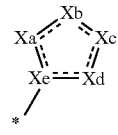

Formula 4B wherein the dotted line ---- can represent a single, or double bond;
Xa is selected from NH, CH, and S;
Xb is selected from C, N, O, and S;
Xc is selected from C, N, O, and S;
Xd is selected from C, N, O, and S;
Xe is selected from C and N;
and * represents point of attachment to NH.

9. The method of claim 1, wherein D is represented by Formula 5B:

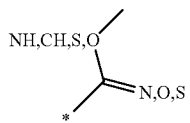

Formula 5B and * represents point of attachment to NH.

10. The method of claim 1, wherein D is represented by Formula 6B:

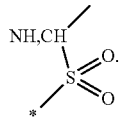

Formula 6B

11. The method of claim 1, wherein D is linked to the NH group via a —$CH_2$— linker.

12. The method of claim 1, wherein the pharmacophore is represented by Formula 8

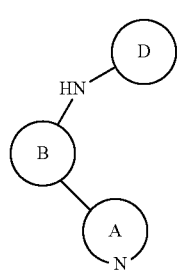

Formula 8 wherein
Ring A is a monocyclic or bicyclic heteroaromatic ring;
Ring B is a non-aromatic or aromatic carbocyclic or heterocyclic group; and
Group D is as defined in any of claims 3-10.

13. The method of claim 1, wherein the pharmacophore is represented by Formula 8

Formula 8

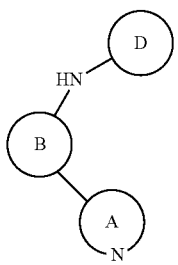

wherein

Ring A is a monocyclic or bicyclic heteroaromatic ring, and wherein Ring A contains a hydrogen bond acceptor;

Ring B is a non-aromatic or aromatic carbocyclic or heterocyclic group;

D is represented by Formula 5B:

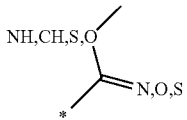

Formula 5B and * represents point of attachment to NH.

14. The method of claim 1, wherein the pharmacophore is represented by Formula 8

Formula 8

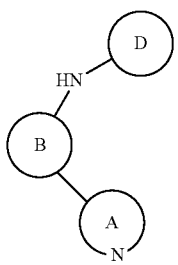

wherein

Ring A is a monocyclic or bicyclic heteroaromatic ring, and wherein Ring A contains a hydrogen bond donor;

Ring B is a non-aromatic or aromatic carbocyclic or heterocyclic group;

D is represented by Formula 5B:

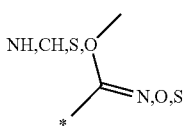

Formula 5B and * represents point of attachment to NH.

15. The method of claim 1, wherein the pharmacophore is represented by Formula 8

Formula 8

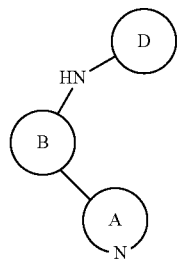

wherein

Ring A is a monocyclic or bicyclic heteroaromatic ring;
Ring B is an aromatic carbocyclic or heterocyclic group;
D is represented by Formula 5B:

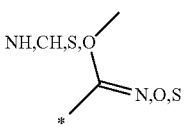

Formula 5B and * represents point of attachment to NH.

16. The method of claim 1, wherein said candidate modulator is an inhibitor of FGFR activity.

17. The method of claim 1, wherein said FGFR is FGFR1, FGFR2 or FGFR3 or FGFR4.

18. The method of claim 17, wherein said candidate modulator interacts with both ASP641 and ALA564.

19. The method of claim 1, wherein said candidate modulator further interacts with one or more additional binding pocket residues of FGFR.

20. The method of claim 19, wherein said binding pocket is one or more of a hinge, gatekeeper, hydrophobic residues, DFG loop or Glycine Rich Loop (GRL) binding pocket(s).

21. The method of claim 19, wherein said binding pocket(s) comprise one or more of the amino acids as set out in Table 8 for FGFR1:

TABLE 8

| Binding pocket | FGFR1 (residue numbering from PDB file: 1AGW) | VEGFR2 (residue numbering from PDB file: 1YWN) |
| --- | --- | --- |
| Hinge | Glu562, Tyr563, Ala564, Ser565 | Glu915, Phe916, Cys917, Lys918 |
| gatekeeper | Val561 | Val914 |
| Hydrophobic residues | Val492, Ala512, Lys514, Leu630, Ala640 | Val846, Ala864, Lys866, Leu1033, Cys1043 |
| DFG loop | Asp641, Phe642, Gly643 | Asp1044, Phe1045, Gly1046 |
| Glycine Rich Loop (GRL) | Leu484, Gly485, Glu486, Gly487, Cys488, Phe489 | Leu838, Gly839, Arg840, Gly841, Ala842, Phe843. |
| Solvent Exposed Area | Lys 482, Leu484, Tyr563, Ser565, Lys566, Gly567, Glu571 | Lys836, Leu838, Phe916, Lys918, Phe919, Gly920, Thr924. |

22. The method of claim 19, wherein said binding pocket is the hinge binding pocket of FGFR comprising amino acids Glu562, Tyr563, Ala564, and Ser565.

23. The method of claim 19, wherein said compound comprises one or more substituents capable of interacting with one or more of the pharmacophoric points as defined in Table 9 below, wherein the type of substituent(s) are as defined in Table 10 below:

TABLE 9

| Pharmacophoric points | Description | Distances from specified C-α atoms of FGFR1 (1AGW PDB Structure) | | |
|---|---|---|---|---|
| P_NH | H-bond to Asp641 Carboxylate | ASP641 5.3 Å | ASN628 6.8 Å | ILE545 8.5 Å |
| P_G5 | H-Bond to Ala564 backbone NH | ALA564 3.6 Å | LEU484 7.5 Å | ALA512 5.5 Å |
| P_D | Pi system favoured for FGFR | ALA640 6.2 Å | LEU630 7.1 Å | ASN628 5.9 Å |
| P_B | Gatekeeper region | VAL561 7.7. Å | ASP641 7.0 Å | LEU630 8.3 Å |
| P_G7 (Optional) | H-Bond to Ala564 backbone C=O | ALA564 4.5 Å | GLY567 4.9 Å | LEU484 6.9 Å |
| P_G6 (Optional) | H-Bond to Glu562 backbone C=O | GLU562 5.6 Å | ALA512 5.2 Å | LEU630 6.8 Å |
| P_Y (Optional) | Solvent exposed area | GLY567 4.5 Å | LEU484 6.1 Å | GLU571 9.1 Å |

TABLE 10

| Pharmacophoric points | Description | Type of Substituent | Tolerance |
|---|---|---|---|
| P_NH | H-bond to Asp 641 Carboxylate | NH | 1 Å |
| P_G5 | H-Bond to Ala564 backbone NH | Hydrogen Bond Acceptor (preferred Aromatic N) | 1 Å |
| P_D | Pi system | sp or sp2 hybridization (preferred sp2) | 2 Å |
| P_B | Gatekeeper region | Aromatic or lipophilic | 2 Å |
| P_G7 (Optional) | H-Bond to Ala564 backbone C=O | Hydrogen Bond Donor (Preferred Aromatic CH or NH) | 1 Å |
| P_G6 (Optional) | H-Bond to GLU562 backbone C=O | Hydrogen Bond Donor (Preferred Aromatic CH or NH) | 1 Å |
| P_Y (Optional) | Solvent exposed area | Lipophilic or aromatic or polar | 2 Å. |

24. The method of claim 1, wherein said step (f) comprises X-ray crystallography, NMR spectroscopy, ITC, thermal denaturation, Mass Spectrometry or SPR binding affinity, or an activity assay.

25. The method of claim 1, wherein step (d) involves fitting of one or more candidate modulators to one or more additional FGFR residues outlined in Table 8:

TABLE 8

| Binding pocket | FGFR1 (residue numbering from PDB file: 1AGW) | VEGFR2 (residue numbering from PDB file: 1YWN) |
|---|---|---|
| Hinge | Glu562, Tyr563, Ala564, Ser565 | Glu915, Phe916, Cys917, Lys918 |

TABLE 8-continued

| Binding pocket | FGFR1 (residue numbering from PDB file: 1AGW) | VEGFR2 (residue numbering from PDB file: 1YWN) |
|---|---|---|
| gatekeeper | Val561 | Val914 |
| Hydrophobic residues | Val492, Ala512, Lys514, Leu630, Ala640 | Val846, Ala864, Lys866, Leu1033, Cys1043 |
| DFG loop | Phe642, Gly643 | Asp1044, Phe1045, Gly1046 |
| Glycine Rich Loop (GRL) | Leu484, Gly485, Glu486, Gly487, Cys488, Phe489 | Leu838, Gly839, Arg840, Gly841, Ala842, Phe843. |
| Solvent Exposed Area | Lys 482, Leu484, Tyr563, Ser565, Lys566, Gly567, Glu571 | Lys836, Leu838, Phe916, Lys918, Phe919, Gly920, Thr924. |

26. The method of claim 1, wherein said candidate modulator is contacted with FGFR and/or VEGFR2 under conditions to determine its function.

27. The method of claim 1, wherein in said step (f), said candidate modulator is contacted with FGFR in the presence of a substrate, and optionally a buffer, to determine the ability of said candidate modulator to inhibit FGFR.

28. The method of claim 1, wherein said FGFR is FGFR1 or FGFR3 which is contacted with said candidate modulator in the presence of a substrate and optionally a buffer.

29. The method of claim 1, wherein said candidate modulator is contacted with FGFR or VEGFR2 under conditions to determine its binding.

30. The method of claim 29, wherein said candidate modulator is contacted with FGFR or VEGFR2 under conditions to determine its binding to FGFR or VEGFR2 using either X-ray crystallography, NMR ligand binding studies, ITC, thermal denaturation, Mass spectrometry or SPR binding affinity measurements.

31. A method for assessing the ability of a candidate modulator to interact with FGFR and/or VEGFR2, which comprises the steps of:
 obtaining or synthesising the candidate modulator identified according to the method of claim 1;
 forming a complex of FGFR and/or VEGFR2 and said candidate modulator; and
 analysing said complex by a physical means to determine the ability of said candidate modulator to interact with FGFR and/or VEGFR2.

32. The method of claim 31, for determining the binding of a candidate modulator to FGFR and/or VEGFR2 by its structure, said method comprising:
 providing a crystal of FGFR and/or VEGFR2;
 soaking the crystal with said candidate modulator to form a complex; and
 determining the structure of said complex.

33. The method of claim 32, for determining the binding of a candidate modulator to FGFR or VEGFR2 by its structure, said method comprising:
 mixing said protein with said candidate modulator to form a protein-candidate modulator complex;
 crystallizing said protein-candidate modulator complex; and
 determining the structure of said protein-candidate modulator complex.

34. The method of claim 31, wherein the physical means for determining the binding of a candidate modulator to FGFR or VEGFR2 is X-ray crystallography, NMR spectroscopy, ITC, thermal denatirisation, Mass spectrometry or SPR.

35. The method of claim 1, further comprising:
 (g) obtaining structural information about the binding of said candidate modulator to FGFR or VEGFR2; and (h) adjusting the structure or functionality of said candidate modulator to improve binding to the binding cavity or cavities.

36. The method of claim 35 which comprises repeating steps (a) to (h) one or more times.

37. A method of identifying a compound which is an inhibitor of FGFR having greater affinity for FGFR than for VEGFR2, having identified a candidate modulator according to claim 1, the method further comprising the steps of:
determining the FGFR activity of the compound; and
determining the VEGFR2 activity of the compound.

38. A method of identifying a compound which is an inhibitor of FGFR having greater affinity for FGFR than for VEGFR2, having identified a candidate modulator according to claim 1, the method further comprising the steps of:
determining the FGFR tyrosine kinase activity of the compound by contacting the compound with the protein under conditions to determine its kinase activity; and
determining the VEGFR2 tyrosine kinase activity of the compound by contacting the compound with the protein under conditions to determine its kinase activity.

39. The method of claim 1, which comprises following identification of a compound, the step of manufacturing the compound or preparing a pharmaceutical composition comprising the compound.

40. A method for preparing a medicament, pharmaceutical composition or drug, the method comprising:
identifying a FGFR candidate modulator according to claim 1;
optimising the structure of said candidate modulator; and
preparing a medicament, pharmaceutical composition or drug containing said optimised candidate modulator.

41. The method of claim 40, wherein optimising the structure of said FGFR candidate modulator comprises:
(i) adding molecular scaffolding; and/or
(ii) adding or varying functional groups; and/or
(iii) connecting the molecule with other molecules such that the chemical structure of the candidate modulator is changed while its original modulating functionality is maintained or enhanced.

42. The method of claim 41, wherein the step of optimising the structure of said FGFR candidate modulator comprises one or more steps selected from the group consisting of:
(i) adding molecular scaffolding to the candidate modulator containing the pharmacophore of Formula 1;
(ii) adding or varying functional groups; and
(iii) connecting the molecule with other molecules such that the chemical structure of the candidate modulator is changed while its original modulating functionality is maintained or enhanced.

43. A method of determining whether a chemical not previously known to be a modulator of FGFR is capable of specifically modulating FGFR comprising:
(a) selecting a compound containing the pharmacophore of Formula 1 as defined in claim 1;
(b) contacting FGFR with a chemical to be tested under conditions such that the compound can interact with FGFR;
(c) detecting the binding and/or modulation of the compound to FGFR; and
(d) identifying chemicals which are capable of binding or modulating FGFR more than VEGFR2.

44. The method of claim 3, wherein the pharmacophore of Formula 1 is an O-substituted thiocarbamate or S-substituted thiocarbamate.

45. The method of claim 5, wherein Formula 2B represents a 1,3,4-thiadiazole or a triazole.

46. The method of claim 18, wherein said candidate modulator binds to said residues via hydrogen bonds.

47. The method of claim 1 or claim 31 further comprising:
obtaining structural information about the binding of said candidate modulator to FGFR or VEGFR2; and
adjusting the structure or functionality of said candidate modulator to improve binding to the binding cavity or cavities.

\* \* \* \* \*